(12) United States Patent
Solinger et al.

(10) Patent No.: US 9,139,646 B2
(45) Date of Patent: *Sep. 22, 2015

(54) METHODS FOR THE TREATMENT OF UVEITIS WITH IL-1β BINDING ANTIBODIES

(71) Applicant: XOMA (US) LLC, Berkeley, CA (US)

(72) Inventors: Alan M. Solinger, Oakland, CA (US); Ahmet Gül, Istanbul (TR)

(73) Assignee: XOMA (US) LLC, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/029,603

(22) Filed: Sep. 17, 2013

(65) Prior Publication Data

US 2014/0242090 A1 Aug. 28, 2014

Related U.S. Application Data

(63) Continuation of application No. 13/102,768, filed on May 6, 2011, now Pat. No. 8,551,487.

(60) Provisional application No. 61/332,658, filed on May 7, 2010, provisional application No. 61/334,125, filed on May 12, 2010, provisional application No. 61/444,638, filed on Feb. 18, 2011.

(51) Int. Cl.
*A61K 39/395* (2006.01)
*C07K 16/24* (2006.01)
*A61K 38/20* (2006.01)
*C07K 16/18* (2006.01)
*A61K 39/00* (2006.01)

(52) U.S. Cl.
CPC .......... *C07K 16/245* (2013.01); *A61K 2039/505* (2013.01); *A61K 2039/54* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 4,762,914 A | 8/1988 | Auron et al. | |
| 4,766,069 A | 8/1988 | Auron et al. | |
| 4,772,685 A | 9/1988 | Schmidt et al. | |
| 4,935,343 A | 6/1990 | Allison et al. | |
| 5,001,057 A | 3/1991 | Auron et al. | |
| 5,077,219 A | 12/1991 | Auron et al. | |
| 5,122,459 A | 6/1992 | Conlon et al. | |
| 5,286,847 A | 2/1994 | Gehrke et al. | |
| 5,348,858 A | 9/1994 | Uetsuki et al. | |
| 5,474,899 A | 12/1995 | Lsi | |
| 5,484,887 A | 1/1996 | Kronheim et al. | |
| 5,510,462 A | 4/1996 | Auron et al. | |
| 5,658,570 A | 8/1997 | Newman et al. | |
| 5,681,933 A | 10/1997 | Auron et al. | |
| 5,766,886 A | 6/1998 | Studnicka et al. | |
| 5,789,185 A | 8/1998 | Lisi | |
| 5,869,619 A | 2/1999 | Studnicka | |
| 5,885,793 A | 3/1999 | Griffiths | |
| 5,959,085 A | 9/1999 | Garrone et al. | |
| 6,899,878 B2 | 5/2005 | Graham et al. | |
| 7,121,691 B2 | 10/2006 | Coushaine et al. | |
| 7,438,910 B2 | 10/2008 | Varnum et al. | |
| 7,531,166 B2 | 5/2009 | Masat et al. | |
| 7,572,770 B2 | 8/2009 | Donath | |
| 7,582,742 B2 | 9/2009 | Masat et al. | |
| 7,695,717 B2 | 4/2010 | Masat et al. | |
| 7,695,718 B2 | 4/2010 | Solinger et al. | |
| 7,744,865 B2 | 6/2010 | Masat et al. | |
| 7,744,866 B2 | 6/2010 | Masat et al. | |
| 7,829,093 B2 | 11/2010 | Masat et al. | |
| 7,829,094 B2 | 11/2010 | Masat et al. | |
| 2003/0022869 A1 | 1/2003 | Wiemer et al. | |
| 2003/0026806 A1 | 2/2003 | Witte et al. | |
| 2003/0124617 A1 | 7/2003 | Gram et al. | |
| 2003/0166069 A1 | 9/2003 | Welcher et al. | |
| 2004/0023869 A1 | 2/2004 | Sims et al. | |
| 2004/0063913 A1 | 4/2004 | Gram et al. | |
| 2005/0084493 A1 | 4/2005 | Witte | |
| 2005/0107399 A1 | 5/2005 | Boman et al. | |
| 2005/0152850 A1 | 7/2005 | Engebretson | |
| 2005/0186615 A1 | 8/2005 | Lin et al. | |
| 2005/0256197 A1 | 11/2005 | Engebretson | |
| 2006/0094663 A1 | 5/2006 | Chemtob | |
| 2007/0065439 A1* | 3/2007 | Green et al. | 424/145.1 |
| 2008/0044414 A1* | 2/2008 | Masat et al. | 424/136.1 |
| 2009/0022733 A1 | 1/2009 | Sims et al. | |
| 2009/0232803 A1 | 9/2009 | Gram et al. | |

(Continued)

FOREIGN PATENT DOCUMENTS

EP 0267611 B1 5/1993
EP 0161901 B1 12/1993

(Continued)

OTHER PUBLICATIONS

Tugal-Tutkun et al, Arthritis and Rheumatism; 2005; vol. 52, No. 8, pp. 2478-2484.*
Markomichelakis et al., "Infliximab versus Corticosteroids for Sight-Threatening Panuveitis Relapse in Behçet's disease: A Comparative 4-week Study," Abstr., EULAR Congress 2010, Ann Rheum Dis. 2010: 69 (Suppl3):76, Rome, Italy 2010.
Marshall SE., "Behçet's disease," Best Pract. Res. Clin. Rheumatol. 18(3):291-311 (2004).
Mat et al. "A double-blind trial of depot corticosteroids in Behçet's syndrome," Rheumatology (Oxford) 45(3):348-352 (2006).
Mochizuki, M., "Immunotherapy for Behçet's Disease," Int. Rev. Immunol. 14(1):49-66 (1997).
Niccoli et al., "Long-term efficacy of infliximab in refractory posterior uveitis of Behçet's disease: a 24-month follow-up study," Rheumatology 46(7):1161-1164 (2007).

(Continued)

*Primary Examiner* — Bridget E Bunner
*Assistant Examiner* — Fozia Hamud
(74) *Attorney, Agent, or Firm* — Jones Day

(57) ABSTRACT

Disclosed are methods and materials for inhibiting (e.g., treating or preventing) uveitis in a subject, including treatment refractory uveitis, using anti-IL-1β binding molecules (e.g., IL-1β binding antibodies or binding fragment thereof).

73 Claims, 10 Drawing Sheets

(56) References Cited

U.S. PATENT DOCUMENTS

| | | | |
|---|---|---|---|
| 2009/0291081 | A1 | 11/2009 | Hsieh et al. |
| 2009/0305992 | A1 | 12/2009 | Donath |
| 2010/0055110 | A1 | 3/2010 | Masat et al. |
| 2010/0061998 | A1 | 3/2010 | Masat et al. |
| 2010/0093636 | A1 | 4/2010 | Schultz et al. |

FOREIGN PATENT DOCUMENTS

| | | |
|---|---|---|
| EP | 0364778 B1 | 3/1996 |
| EP | 0 569 687 B1 | 8/2002 |
| WO | 95/01997 A1 | 1/1995 |
| WO | 02/16436 A2 | 2/2002 |
| WO | 03/010282 A2 | 2/2003 |
| WO | 03/034984 A2 | 5/2003 |
| WO | 03/073982 A2 | 9/2003 |
| WO | 2004/002512 A1 | 1/2004 |
| WO | 2004022718 A2 | 3/2004 |
| WO | 2004/067568 A2 | 8/2004 |
| WO | 2004/072116 A2 | 8/2004 |
| WO | 2005019259 A2 | 3/2005 |
| WO | 2005084696 A1 | 9/2005 |
| WO | 2006081139 A2 | 8/2006 |
| WO | 2007002261 A2 | 1/2007 |
| WO | 2007/042524 A2 | 4/2007 |
| WO | 2007/120828 A1 | 10/2007 |
| WO | 2008/077145 A2 | 6/2008 |

OTHER PUBLICATIONS

Nussenblatt, R.B., "Uveitis in Behçet's Disease," Int. Rev. Immunol. 14(1):67-79 (1997).
Ohno et al., "Efficacy, Safety, and Pharmacokinetics of Multiple Administration of Infliximab in Behçet's Disease with Refractory Uveoretinitis," J. Rheumatol. 31(7):1362-1368 (2004).
Okada, A.A., "Immunomodulatory Therapy for Ocular Inflammatory Disease: A Basic Manual and Review of the Literature," Ocul. Immunol. Inflamm. 13(5):335-351 (2005).
Opremcak, E.M., Symptoms and signs of uveitis. In: Uveitis: A Clinical Manual for Ocular Inflammation Eds. (1995) New York, Springer-Verlag, 14-30.
Pay et al., "Synovial proinflammatory cytokines and their correlation with matrix metalloproteinase-3 expression in Behçet's disease," Rheumatology 26(7):608-613 (2006).
Pipitone et al., "New approaches in the treatment of Adamantiades-Behçet's disease," Curr. Opin. Rheumatol; 2006 18(1):3-9, Lippincott Williams & Wilkins.
Planck et al., "Cytokine mRNA Levels in Rat Ocular Tissues After Systemic Endotoxin Treatment," Invest. Ophthalmol. Vis. Sci. 35(3):924-930 (1994).
Rosenbaum, J.T., "Future for biological therapy for uveitis," Curr. Opin. Ophthalmol. 221(6):473-477 (2010).
Rosenbaum, J.T., "Uveitis: Treatment. In: UpToDate," Basow DS, eds. Waltham, MA, www.UpToDate.com., Oct. 2009.
Seyahi et al., "Clinical Features and Diagnosis of Behçet's Syndrome," Int. J. Adv. Rheumatol. 5(1):8-13 (2007).
Sijssens et al., "Distinct Cytokine Patterns in the Aqueous Humor of Children, Adolescents and Adults with Uveitis," Ocul. Immunol. Inflamm. 16(5):211-216 (2008).
Teoh et al., "Tailoring biological treatment: anakinra treatment of posterior uveitis associated with the CINCA syndrome," Br. J. Ophthalmol. 91(2):263-264 (2007).
Thurau et al., Uveitis and Immunological Disorders (Essentials in Ophthalmology); Chpt 16: Immunomodulatory Therapy in Uveitis, Pleyer U and Mondino B, eds. Berlin, Germany, Springer-Verlag Heidelberg. NY (2005) 255-271, Germany.
Tsai, M.L., "Suppression of experimental uveitis by a recombinant adeno-associated virus vector encoding interleukin-1 receptor antagonist," Mol. Vis. 15:1542-1552 (2009).
Tugal-Tutkun et al., "Uveitis in Behcet Disease: An Analysis of 880 Patients," Am. J. Ophthalmol. 138(3):373-380 (2004).
Tugal-Tutkun I., "Behçet's Uveitis," Middle East Afr. J. Ophthalmol. 16(4):219-224 (2009).
Valentincic et al., "Intraocular and serum cytokine profiles in patients with intermediate uveitis," Mol. Vis. 17:2003-2010 (2011).
Botsios et al., "Efficacy of the IL-1 receptor antagonist, anakinra, for the treatment of diffuse anterior scleritis in rheumatoid arthritis. Report of two cases," Rheumatology 46(6):1042-1043 (2007).
Botsios et al., "Resistant Behçet disease responsive to anakinra," Ann. Intern. Med. 149(4):284-286 (2008).
Horai et al., "Cytokines in Autoimmune Uveitis," J. Interferon Cytokine Res. 31(10):733-744 (2011).
PCT International Search Report for PCT/US11/35646 mailed on Oct. 19, 2011.
Benitez-Del-Castillo et al., "Long-term treatment of refractory posterior uveitis with anti-TNFα (infliximab)," Eye 19:841-845 (2005).
Cantarini et al., "Successful use of canakinumab in a patient with resistant Behçet's disease," Clin. Exp. Rheumatol. 30(3 Suppl 72):S115 (2012) (Epub Sep. 25, 2012).
Simonini et al., "Clinical and transcriptional response to the long-acting interleukin-1 blocker canakinumab in Blau syndrome-related uveitis," Arthritis Rheum. 65(2):513-518 (2013).
Tappeiner et al., "New biologic drugs: anti-interleukin therapy," Dev. Ophthalmol. 51:79-89 (2012) (Epub Apr. 17, 2012).
Tsai et al., "Suppression of experimental uveitis by a recombinant adeno-associated virus vector encoding interleukin-1 receptor antagonist," Mol. Vis. 15:1542-1552 (2009).
Ugurlu et al., "Canakinumab in a patient with juvenile Behcet's syndrome with refractory eye disease," Ann. Rheum. Dis. 71(9):1589-1591 (2012) (Epub May 14, 2012).
Dinarello, "Biologic basis for interleukin-1 in disease", Blood, J. Amer. Soc. Hematology 87(6):2095-2147 (1996).
Dinarello, "The many worlds of reducing interleukin-1," Arthritis Rheum. 52:1960-1967 (2005).
Pascual et al., "Role of interleukin-1 (IL-1) in the pathogenesis of systemic onset juvenile idiopathic arthritis and clinical response to IL-1 blockade", J. Exper. Med. 201(9):1479-1486 (2005).
Dinarello, "Therapeutic strategies to reduce IL-1 activity in treating local and systemic inflammation," Curr. Opin. Pharmacol. 4:378-385 (2004).
Haraoui et al., "Biologic agents in the treatment of rheumatoid arthritis," Curr. Pharm. Biotechnol. 1:217-233 (2000).
Dayer, "The pivotal role of interleukin-1 in the clinical manifestations of rheumatoid arthritis," Rheumatology 42 (Suppl.2):ii3-ii10 (2003).
Joosten et al., "IL-1abeta blockade prevents cartilage and bone destruction in murine type II collagen-induced arthritis, whereas TNF-a blockade only ameliorates joint inflammation," J. Immunol. 163:5049-5055 (1999).
Wooley et al., "The effect of an interleukin-1 receptor antagonist protein on type II collagen-induced arthritis and antigen-induced arthritis in mice," Arthritis Rheum. 36(9):1305-1314 (1993).
Inoue et al., "Efficacy of daily compared to intermittent administration of IL-1Ra for protection against bone and cartilage destruction in collagen-challenged mice," Clin. Exp. Rheumatol. 21(1):33-39 (2003).
Bresnihan et al., "Treatment of rheumatoid arthritis with recombinant human interleukin-1 receptor antagonist," Arthritis Rheum. 41(12):2196-2204 (1998).
Jacques et al., "The role of IL-1 and IL-Ra in joint inflammation and cartilage degradation," Vitam. Horm. 74:371-404 (2006).
Keystone EC and Strond V, Emerging Therapies in Rheumatoid Arthritis. In: Kelley's Textbook of Rheumatology. Harris E, Jr., M.D., Budd R, M.D., Genovese M, M.D., Firestein GS, M.D., Sargent J, M.D. and Sledge C, M.D., eds. Philadelphia, Elsevier Saunders (2005) 951-60 (chapter 62).
Joosten et al., "Anticytokine treatment of established type II collagen-induced arthritis in DBA/1 mice. A comparative study using anti-TNF alpha, anti-IL-1 alpha/beta, and IL-1Ra," Arthritis Rheum. 39(5):797-809 (1996).
Punzi et al., "Pro-inflammatory interleukins in the synovial fluid of rheumatoid arthritis associated with joint hypermobility," Rheumatology 40:202-204 (2001).
Lovell et al., "Preliminary evidence for bioactivity of IL-1 trap (rilonacept), a long acting IL-1 inhibitor, in systemic juvenile idiopathic arthritis (sJIA)," Arthritis Rheum. 54(9) (2006).

(56) References Cited

OTHER PUBLICATIONS

Firestein GS., "Rheumatoid Arthritis," ACPMedicine. (2007) 15(II):1-18 (in two parts).
Harris et al., "Overview of the management of rheumatoid arthritis," UptoDate®. Feb. 4, 2008.
Akman et al., "Relationship between periodontal findings and specific polymorphisms of interleukin-1α and -1β in Turkish patients with Behçet's disease," Arch. Dermatol. Res. 300:19-26 (2008).
Altenberg et al., "Epidemiology and clinical manifestations of Adamantiades-Behçet disease in Germany—Current pathogenetic concepts and therapeutic possibilities," J. Dtsch. Dermatol. Ges. 4(1):49-65 (2006).
Barnes CG., "Treatment of Behçet's syndrome," Rheumatology (Oxford) 45(3):245-247 (2006).
Becker, MD., "Management of sight-threatening uveitis: new therapeutic options," Drugs 65(4):497-519 (2005).
Benitez-Del-Castillo et al., "Long-term treatment of refractory posterior uveitis with anti-TNFα (infliximab)," Eye 19(8):841-845 (2005).
Brito et al., "IL-1 and TNF Receptor-Deficient Mice Show Decreased Inflammation in an Immune Complex Model of Uveitis," Invest. Ophthalmol. Vis. Sci. 40(11):2583-2589 (1999).
Buggage, R.R., "A Double-masked, Randomized Study to Investigate the Safety and Efficacy of Daclizumab to Treat the Ocular Complications Related to Behçet's Disease," Ocul. Immunol. Inflamm. 15(2):63-70 (2007).
Dana, R., "Comparison of Topical Interleukin-1 vs Tumor Necrosis Factor-Alpha Blockade with Corticosteroid Therapy on Murine Corneal Inflammation, Neovascularization, and Transplant Survival (an American Ophthalmological Society thesis)," Trans. Am. Ophthalmol. Soc. 105:330-343 (2007).
Deschenes et al., "International Uveitis Study Group (IUSG): Clinical Classification of Uveitis," Ocul. Immunol. Inflamm. 16(1):1-2 (2008).
Dinarello, C.A., "The Many Worlds of Reducing Interleukin-1," Arthritis Rheum. 52(7):1960-1967 (2005).
Durrani et al., "Uveitis: A Potentially Blinding Disease," Ophthalmologica 218(4):223-236 (2004).
Evereklioglu C., "Managing the symptoms of Behcet's disease," Expert Opin. Pharmacother. 5(2):317-328 (2004).
Foxman et al., "Inflammatory Mediators in Uveitis: Differential Induction of Cytokines and Chemokines in Th1- versus Th2-mediated Ocular Inflammation," J. Immunol. 168(5):2483-2492 (2002).
Franks et al., "Cytokines in human intraocular inflammation," Curr. Eye Res. 11 Suppl:187-191 (1992).
Gül et al., Safe, Rapid-onset, and Sustained Biological Activity of IL-1 Beta Regulating Antibody XOMA 052 in Resistant Uveitis of Behçet's Disease: Preliminary Results of a Pilot Trial., Abstract., The Annual European Congress of Rheumatology (EULAR2010-SCIE-5093), Rome, Italy 2010; Ann. Rheum. Dis. 2010; 69(Suppl 3):178.
Gül et al., "Interleukin-1β-regulating antibody XOMA 052 (gevokizumab) in the treatment of acute exacerbations of resistant uveitis of Behçet's disease: an open-label pilot study," Annals of the Rheumatic Diseases 71:563-566 (2012).
Gül, A., "Behçet's Disease as an Autoinflammatory Disorder," Curr. Drug Targets—Inflammatory & Allergy, 4:81-83 (2005).
Hashimoto et al., "Treatment of Behçet's disease," Curr. Opin. Rheumatol. 4(1):31-34 (1992).
Hatemi et al., "EULAR recommendations for the management of Behçet disease," Ann. Rheum. Dis. 67 (12):1656-1662 (2008).
Hatemi et al., "Management of Behçet disease: a systematic literature review for the European League Against Rheumatism evidence-based recommendations for the management of Behçet disease," Ann. Rheum. Dis. 68 (10):1528-1534 (2009).
Jabs et al., "Guidelines for the Use of Immunosuppressive Drugs in Patients With Ocular Inflammatory Disorders: Recommendations of an Expert Panel," Am. J. Ophthalmol. 130(4):492-513 (2000).
Jabs et al., "Standardization of Uveitis Nomenclature for Reporting Clinical Data. Results of the First International Workshop., (SUN) working group," Am. J. Ophthalmol. 140:509-516 (2005).
Kaklamani et al., "Treatment of Behçet's disease—an update," Semin. Arthritis Rheum. 30(5):299-312 (2001).
Keane-Myers et al., "Prevention of Allergic Eye Disease by Treatment with IL-1 Receptor Antagonist," Invest. Ophthalmol. Vis. Sci. 40(12):3041-3046 (1999).
Keino et al., "Clinical features and visual outcomes of Japanese patients with scleritis," Br. J. Ophthalmol. 94:1459-1463 (2010).
Keino et al., "Frequency and clinical features of intraocular inflammation in Tokyo," Clinical & Experimental. Ophthalmology. 37:595-601 (2009).
Keino et al., "Effect of Infliximab on Gene Expression Profiling in Behçet's Disease," Invest. Ophthalmol. Vis. Sci. 52 (10):7681-7686 (2011).
Kempen et al., "Randomized Comparison of Systemic Anti-inflammatory Therapy Versus Fluocinolone Acetonide Implant for Intermediate, Posterior, and Panuveitis: The Multicenter Uveitis Steroid Treatment Trial," Ophthalmology 18 (10)1916-1926 (2011).
Kitamei et al., "Clinical features of intraocular inflammation in Hokkaido," Japan Acta Ophthalmol. 87(4):424-428 (2009).
Kuiper, J.J., "Intraocular interleukin-17 and Proinflammatory Cytokines in HLA-A29-Associated Birdshot Chorioretinopathy," Am. J. Ophthalmol. 152(2):177-182 e1 (2011).
Kurup, S.K., "Immunotherapeutic approaches in ocular inflammatory diseases," Arch. Immunol. Ther. Exp. (Warsz) 53(6):484-496 (2005).
Lachmann et al., "The Emerging Role of Interleukin-1β in Autoinflammatory Diseases," Arthritis Rheum. 63 (2):314-324 (2011).
Luna et al., "Blood-Retinal Barrier (BRB) Breakdown in Experimental Autoimmune Uveoretinitis: Comparison with Vascular Endothelial Growth Factor, Tumor Necrosis Factor Alpha, and Interleukin-1β-Mediated Breakdown," J. Neurosci. Res. 49(3):268-280 (1997).

\* cited by examiner

Figure 1

| Patient | Colchicine | AZA | CysA | PRD |
|---|---|---|---|---|
| 1001 | - | + | + | 10 |
| 1002 | - | + | - | 7.5 |
| 1003 | + | + | + | 10 |
| 1004 | - | + | + | 5 |
| 1005 | - | + | - | 5 |
| 1006 | + | + | + | 20 |
| 1007 | - | + | + | 10 |

Figure 2

| 1001 | Right Eye | | | | | |
|---|---|---|---|---|---|---|
| Days | Visual Acuity | Ant. Chamber cells | Flare Score | Vitreous haze | Ben Ezra Score | Other |
| Screen | 20/63 | 4+ | 610 | 3+ | 7 | Hypopyon uveitis attack |
| Day 0 | 20/63 | 4+ | 467 | 3+ | 8 | |
| Day 1 | 20/100 | 4+ | 45 | 3+ | 4 | |
| Day 4 | 20/50 | 4+ | 62 | 2+ | 4 | |
| Day 7 | 20/50 | 3+ | 51 | 1+ | 3 | |
| Day 14 | 20/32 | 3+ | 25 | 0.5 | 3 | |
| Day 21 | 20/20 | 0.5 | 28 | 0 | 0 | |
| Day 28 | 20/20 | 0 | 29 | 0.5 | 0 | |
| Day 56 (55) | 20/20 | 0 | 13 | 0 | 0 | |
| Day 57 (56) | 20/20 | 0 | 11 | 0 | 0 | 2nd infusion |
| Day 58 (57) | 20/20 | 0 | 15 | 0 | 0 | |
| Day 64 | 20/20 | 0 | 17 | 0 | 0 | |
| Day 98 | 20/20 | 0 | 12 | 0 | 0 | |

| 1001 | Left Eye | | | | | |
|---|---|---|---|---|---|---|
| Days | Visual Acuity | Ant. Chamber cells | Flare Score | Vitreous haze | Ben Ezra Score | Other |
| Screen | 20/32 | 1+ | 10 | 0.5 | 1 | No obvious attack |
| Day 0 | 20/32 | 1+ | 20 | 0.5 | 1 | |
| Day 1 | 20/32 | 1+ | 17 | 0.5 | 1 | |
| Day 4 | 20/32 | 0 | 21 | 0 | 0 | |
| Day 7 | 20/32 | 0 | 21 | 0 | 0 | |
| Day 14 | 20/32 | 2+ | 10 | 0.5 | 0 | |
| Day 21 | 20/25 | 0 | 14 | 0 | 0 | |
| Day 28 | 20/25 | 0 | 22 | 0 | 0 | |
| Day 56 (55) | 20/32 | 2+ | 14 | 0 | 1 | Retinitis attack |
| Day 57 (56) | 20/32 | 0.5 | 20 | 0 | 1 | 2nd infusion |
| Day 58 (57) | 20/25 | 0.5 | 20 | 0 | 1 | |
| Day 64 | 20/25 | 0 | 16 | 0 | 1 | |
| Day 98 | 20/32 | 0 | 15 | 0 | 0 | |

Figure 3

| 1002 | Right Eye | | | | | |
|---|---|---|---|---|---|---|
| Days | Visual Acuity | Ant. Chamber cells | Flare Score | Vitreous haze | Ben Ezra Score | Other |
| Screen | 20/25 | 0 | 5 | 0 | 5 | Retinal infiltrates, inflammatory sheating |
| Day 0 | 20/20 | 0.5 | 4 | 0 | 7 | |
| Day 1 | 20/20 | 0.5 | 5 | 0 | 5 | |
| Day 4 | 20/20 | 0.5 | 5 | 0 | 2 | |
| Day 7 | 20/20 | 0.5 | 5 | 0 | 0 | |
| Day 14 | 20/20 | 0.5 | 5 | 0 | 0 | |
| Day 21 | 20/20 | 0.5 | 5 | 0 | 0 | |
| Day 28 | 20/20 | 0 | 4 | 0 | 0 | Retinal infiltrates |
| Day 56 | 20/20 | 0 | 7 | 0 | 1 | 2nd infusion |
| Day 57 | 20/20 | 0 | 9 | 0 | 1 | |
| Day 60 | 20/20 | 0 | 8 | 0 | 0 | |
| Day 98 (102) | 20/20 | 2+ | 9 | 0 | 1 | Small retinal infiltrate |

| 1002 | Left Eye | | | | | |
|---|---|---|---|---|---|---|
| Days | Visual Acuity | Ant. Chamber cells | Flare Score | Vitreous haze | Ben Ezra Score | Other |
| Screen | 20/20 | 0 | 3 | 0 | 0 | No active disease |
| Day 0 | 20/20 | 0 | 3 | 0 | 0 | |
| Day 1 | 20/20 | 0 | 4 | 0 | 0 | |
| Day 4 | 20/20 | 0 | 5 | 0 | 0 | |
| Day 7 | 20/20 | 0 | 5 | 0 | 0 | |
| Day 14 | 20/20 | 0 | 3 | 0 | 0 | |
| Day 21 | 20/20 | 0 | 6 | 0 | 0 | |
| Day 28 | 20/20 | 0 | 3 | 0 | 0 | |
| Day 56 | 20/20 | 0 | 5 | 0 | 0 | |
| Day 57 | 20/20 | 0 | 5 | 0 | 0 | 2nd infusion |
| Day 60 | 20/20 | 0 | 5 | 0 | 0 | |
| Day 98 | 20/20 | 0 | 4 | 0 | 0 | |

Figure 4

| 1003 | Right Eye | | | | | |
|---|---|---|---|---|---|---|
| Days | Visual Acuity | Ant. Chamber cells | Flare Score | Vitreous haze | Ben Ezra Score | Other |
| Screen | | | | | | Not examined |
| Day 0 | | | | | | No light perception |
| Day 1 | | | | | | |
| Day 4 | | | | | | |
| Day 7 | | | | | | |
| Day 14 | | | | | | |
| Day 21 | | | | | | |
| Day 28 | | | | | | |
| Day 56 | | | | | | |
| Day 98 | | | | | | |

| 1003 | Left Eye | | | | | |
|---|---|---|---|---|---|---|
| Days | Visual Acuity | Ant. Chamber cells | Flare Score | Vitreous haze | Ben Ezra Score | Other |
| Screen | CF from 2 meters | 3+ | 43 | 2+ | 1 | |
| Day 0 | CF from 2 meters | 3+ | 39 | 0.5 | 0 | |
| Day 1 | 20/200 | 2+ | 26 | 0.5 | 0 | |
| Day 4 | 20/200 | 1+ | 22 | 1+ | 0 | |
| Day 7 | 20/125 | 1+ | 18 | 0.5 | 0 | |
| Day 14 | 20/125 | 0 | 28 | 0.5 | 0 | |
| Day 21 | 20/125 | 1+ | 32 | 0.5 | 0 | |
| Day 28 | 20/125 | 1+ | 31 | 0.5 | 0 | |
| Day 56 | 20/100 | 1+ | 38 | 0.5 | 0 | |
| Day 98 | 20/200 | 0.5 | 28 | 0.5 | 0 | |

Figure 5

| 1004 | Right Eye | | | | | |
|---|---|---|---|---|---|---|
| Days | Visual Acuity | Ant. Chamber cells | Flare Score | Vitreous haze | Ben Ezra Score | Other |
| Screen | 20/32 | 0.5 | 9 | 0.5 | 4 | |
| Day 0 | 20/32 | 0.5 | 9 | 0.5 | 3 | |
| Day 1 | 20/25 | 0.5 | 7 | 0.5 | 3 | |
| Day 4 | 20/25 | 0 | 6 | 0 | 2 | |
| Day 7 | 20/25 | 0 | 7 | 0 | 0 | |
| Day 14 | 20/25 | 0 | 7 | 0 | 0 | |
| Day 21 | 20/25 | 0 | 7 | 0 | 0 | |
| Day 25 | 20/25 | 0 | 7 | 0 | 0 | |
| Day 28 | 20/25 | 0 | 10 | 0 | 0 | |
| Day 56 | 20/25 | 0 | 5 | 0 | 0 | |
| Day 95 | 20/32 | 0 | 5 | 0 | 2 | Retinitis attack |
| Day 98 | 20/50 | 0.5 | 6 | 0.5 | 1 | |
| Day 98+4 | 20/40 | 0 | 4 | 0.5 | 0 | |

| 1004 | Left Eye | | | | | |
|---|---|---|---|---|---|---|
| Days | Visual Acuity | Ant. Chamber cells | Flare Score | Vitreous haze | Ben Ezra Score | Other |
| Screen | 20/63 | 1+ | 13 | 1+ | 0 | macula is not visible, inferior precipitates |
| Day 0 | 20/63 | 4+ | 60 | 1+ | 0 | macula is not visible, inferior precipitates |
| Day 1 | 20/50 | 3+ | 30 | 1+ | 0 | macula is not visible, inferior precipitates |
| Day 4 | 20/25 | 2+ | 13 | 0.5 | 0 | |
| Day 7 | 20/25 | 1+ | 11 | 0.5 | 0 | |
| Day 14 | 20/25 | 1+ | 10 | 1+ | 0 | |
| Day 21 | 20/25 | 1+ | 13 | 0.5 | 2 | Possible retinitis attack |
| Day 25 | 20/32 | 2+ | 11 | 1+ | 3 | Retinitis attack |
| Day 28 | 20/25 | 1+ | 7 | 1+ | 3 | Retinitis attack |
| Day 56 | 20/20 | 0 | 6 | 0 | 0 | |
| Day 95 | CF 1 m | 4+ | 56 | 1+ | 11 | Retinitis attack |
| Day 98 | CF 50 cm | 3+ | 19 | 1+ | 7 | |
| Day 98+4 | 20/200 | 2+ | 12 | 1+ | 5 | |

Figure 6

| 1005 | Right Eye | | | | | |
|---|---|---|---|---|---|---|
| Days | Visual Acuity | Ant. Chamber cells | Flare Score | Vitreous haze | Ben Ezra Score | Other |
| Screen | Hand Movement (HM) | 3+ | 60 | 0.5 | 12 | Diffuse retinal edema, serious retinal detachment/diffuse infiltration |
| Day 0 | HM/CF 0.2 m | 4+ | 60 | 0.5 | 12 | |
| Day 1 | CF 0.5 m | 3+ | 51 | 0.5 | 7 | |
| Day 4 (3) | CF 1 m | 2+ | 40 | 0.5 | 0 | macular hole, pale optic disc |
| Day 7 | CF 2 m | 0.5 | 30 | 0 | 0 | |
| Day 14 | 20/25 | 0 | 27 | 0.5 | 0 | macular hole |
| Day 21 | CF 0.5m | 0 | 23 | 0 | 0 | macular hole |
| Day 28 | CF 1 m | 0 | 20 | 0 | 0 | macular hole |
| Day 29 | | | | | | 2nd infusion |
| Day 42 | 20/200 | 0 | 19 | 0 | 0 | macular hole |
| Day 56 | CF 3m | 0 | 19 | 0 | 0 | macular hole |
| Day 98(97) | CF 5m | 0 | 12 | 0 | 0 | macular hole |

| 1005 | Left Eye | | | | | |
|---|---|---|---|---|---|---|
| Days | Visual Acuity | Ant. Chamber cells | Flare Score | Vitreous haze | Ben Ezra Score | Other |
| Screen | 20/20 | 0 | 16 | 0 | 0 | No obvious attack |
| Day 0 | 20/20 | 0 | 21 | 0 | 0 | |
| Day 1 | 20/20 | 0 | 18 | 0 | 0 | |
| Day 4 (3) | 20/20 | 0 | 9 | 0 | 0 | |
| Day 7 | 20/20 | 0 | 20 | 0 | 1 | macular edema |
| Day 14 | 20/20 | 0 | 20 | 0 | 0 | cystoid macular edema |
| Day 21 | 20/20 | 0 | 18 | 0 | 0 | cystoid macular edema |
| Day 28 | 20/20 | 0 | 14 | 0 | 0 | cystoid macular edema |
| Day 29 | | | | | | |
| Day 42 | 20/20 | 0 | 14 | 0 | 0 | |
| Day 56 | 20/20 | 0 | 11 | 0 | 0 | |
| Day 98(97) | 20/20 | 0 | 8 | 0 | 0 | |

Figure 7

| 1006 | Right Eye | | | | | |
|---|---|---|---|---|---|---|
| Days | Visual Acuity | Ant. Chamber cells | Flare Score | Vitreous haze | Ben Ezra Score | Other |
| Screen | 20/32 | 4+ | 20 | 1+ | 8 | |
| Day 0 | 20/32 | 4+ | 20 | 1+ | 7 | |
| Day 1 | 20/40 | 3+ | 13 | 1+ | 7 | |
| Day 4 (5) | 20/32 | 2+ | 24 | 1+ | 3 | |
| Day 7 | 20/32 | 0.5 | 23 | 0.5 | 1 | |
| Day 14 | 20/25 | 0 | 22 | 0.5 | 0 | |
| Day 21 | 20/32 | 0 | 18 | 0.5 | 0 | |
| Day 28 | 20/20 | 0 | 18 | 0 | 0 | |
| Day 49 | 20/32 | 2+ | 11 | 0.5 | 6 | Occulsive vasculitis, 2nd infusion |
| Day 56 | 20/32 | 2+ | 19 | 1+ | 3 | Regressing vasculitis, sheating, hemmorhages |
| Day 90 | Hand movement | 3+ | 13 | 0.5 | 9 | New uveitis attack |
| Day 98(96) | Hand movement | 0 | 23 | 0.5 | 9 | |

| 1006 | Left Eye | | | | | |
|---|---|---|---|---|---|---|
| Days | Visual Acuity | Ant. Chamber cells | Flare Score | Vitreous haze | Ben Ezra Score | Other |
| Screen | 20/20 | 1+ | 7 | 0 | 0 | |
| Day 0 | 20/20 | 1+ | 7 | 0 | 0 | |
| Day 1 | 20/20 | 1+ | 6 | 0 | 0 | |
| Day 4 (5) | 20/20 | 0 | 12 | 0 | 0 | |
| Day 7 | 20/20 | 0 | 12 | 0 | 0 | |
| Day 14 | 20/20 | 0 | 11 | 0 | 0 | |
| Day 21 | 20/20 | 0.5 | 8 | 0 | 0 | |
| Day 28 | 20/20 | 0 | 7 | 0 | 1 | Superficial retinal infiltrate |
| Day 49 | 20/20 | 0.5 | 7 | 0 | 0 | |
| Day 56 | 20/20 | 0.5 | 5 | 0 | 1 | Small retinal infiltrate |
| Day 90 | 20/20 | 0 | 3 | 0 | 0 | |
| Day 98(96) | 20/20 | 0 | 6 | 0 | 0 | |

Figure 8

| 1007 | Right Eye | | | | | |
|---|---|---|---|---|---|---|
| Days | Visual Acuity | Ant. Chamber cells | Flare Score | Vitreous haze | Ben Ezra Score | Other |
| Screen | 20/200 | 2+ | 18 | 0.5 | 0 | |
| Day 0 | 20/200 | 3+ | 25 | 0.5 | 0 | |
| Day 1 | 20/100 | 3+ | 25 | 0.5 | 0 | |
| Day 4 (3) | 20/100 | 0.5+ | 23 | 0.5 | 0 | |
| Day 7 | 20/100 | 0 | 26 | 0.5 | 0 | |
| Day 14 | 20/100 | 0.5+ | 17 | 0.5 | 0 | |
| Day 21 | 20/125 | 0 | 17 | 0.5 | 0 | |
| Day 22 | | | | | | macular scar + ERM + CME |
| Day 28 | 20/125 | 0 | 16 | 0.5 | 1 | |
| Day 56 | 20/125 | 0.5 | 23 | 0.5 | 0 | |
| Day 98(97) | 20/100 | 2+ | 7 | 0.5 | 0 | |

| 1007 | Left Eye | | | | | |
|---|---|---|---|---|---|---|
| Days | Visual Acuity | Ant. Chamber cells | Flare Score | Vitreous haze | Ben Ezra Score | Other |
| Screen | 20/200 | 4+ | 21 | 2+ | 3 | |
| Day 0 | 20/200 | 4+ | 23 | 1+ | 3 | |
| Day 1 | 20/100 | 3+ | 23 | 1+ | 3 | |
| Day 4 | 20/100 | 1+ | 21 | 1+ | 2 | |
| Day 7 | 20/100 | 0.5 | 21 | 0.5 | 1 | Cystoid macular edema |
| Day 14 | 20/100 | 0 | 18 | 0.5 | 1 | Cystoid macular edema |
| Day 21 | 20/100 | 0 | 14 | 0.5 | 1 | Cystoid macular edema |
| Day 22 | | | | | | Intravitreal steroid for CME |
| Day 28 | 20/100 | 0 | 11 | 0.5 | 1 | ERM |
| Day 56 | 20/63 | 0 | 8 | 0.5 | 0 | |
| Day 98(97) | 20/63 | 0 | 11 | 0.5 | 0 | |

Figure 9
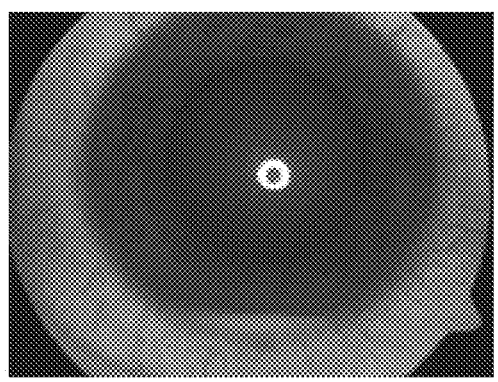
Screen
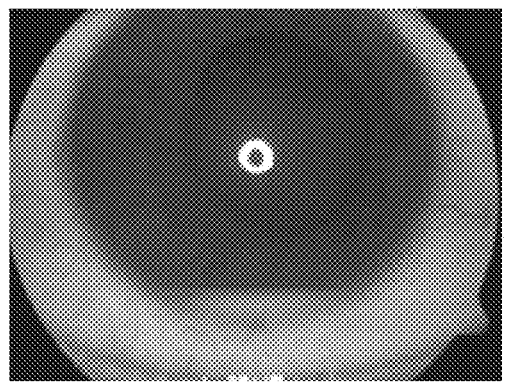
Day 0
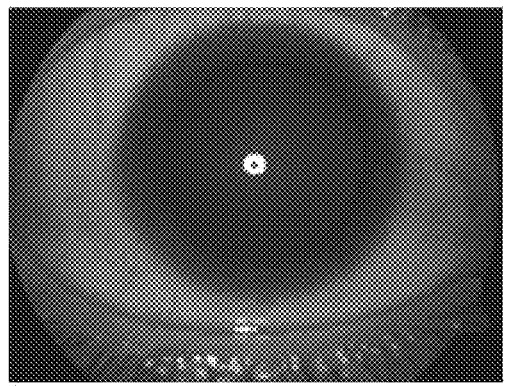
Day 1
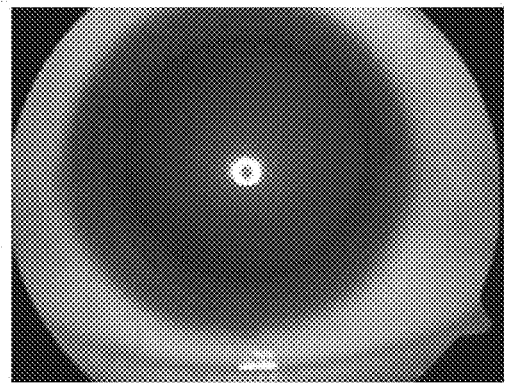
Day 4

Figure 10
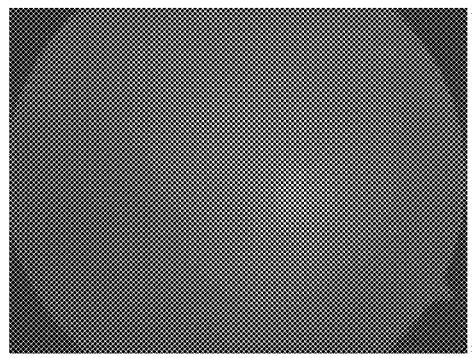
Day 0
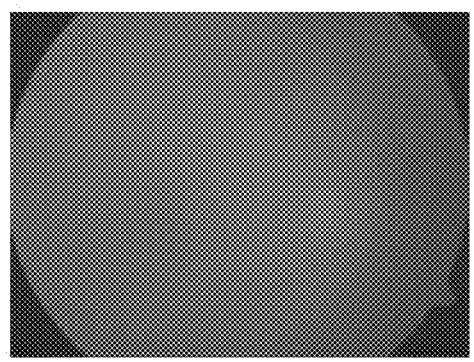
Day 1
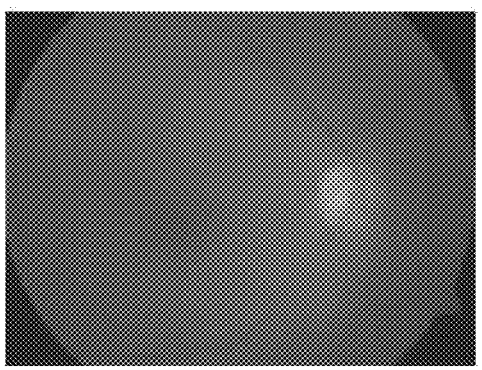
Day 4
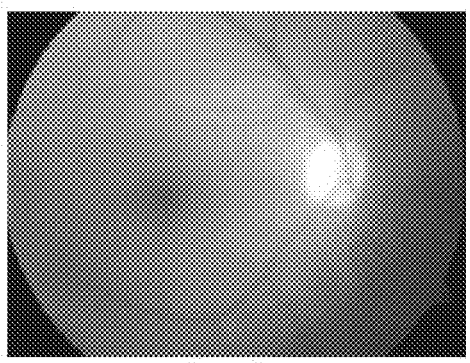
Day 7
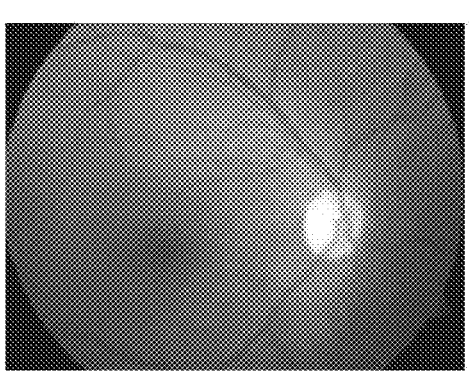
Day 14
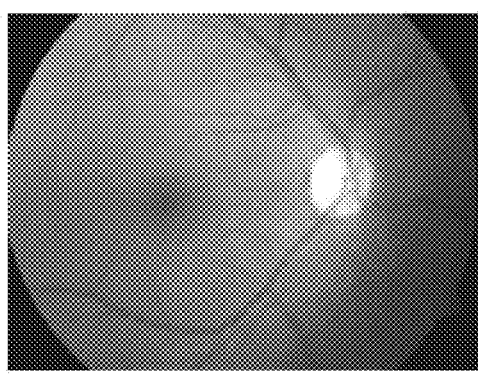
Day 21

SEQUENCE LISTING

```
<160> NUMBER OF SEQ ID NOS: 6

<210> SEQ ID NO 1
<211> LENGTH: 23
<212> TYPE: PRT
<213> ORGANISM: Artificial
<220> FEATURE:
<223> OTHER INFORMATION: Synthesized- epitope

<400> SEQUENCE: 1

Glu Ser Val Asp Pro Lys Asn Tyr Pro Lys Lys Lys Met Glu Lys Arg
1               5                   10                  15

Phe Val Phe Asn Lys Ile Glu
            20

<210> SEQ ID NO 2
<211> LENGTH: 5
<212> TYPE: PRT
<213> ORGANISM: Artificial
<220> FEATURE:
<223> OTHER INFORMATION: Synthesized- linker

<400> SEQUENCE: 2

Gly Gly Gly Gly Ser
1               5

<210> SEQ ID NO 3
<211> LENGTH: 107
<212> TYPE: PRT
<213> ORGANISM: Artificial
<220> FEATURE:
<223> OTHER INFORMATION: Synthesized- AB5 light chain varaible region

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Leu Gln Gly Lys Met Leu Pro Trp
                85                  90                  95

Thr Phe Gly Gly Gly Thr Lys Leu Glu Ile Lys
            100                 105

<210> SEQ ID NO 4
<211> LENGTH: 120
<212> TYPE: PRT
<213> ORGANISM: Artificial
<220> FEATURE:
<223> OTHER INFORMATION: Synthesized- AB5 heavy chain variable region

<400> SEQUENCE: 4

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
```

```
                    20                  25                  30
Gly Met Gly Val Gly Trp Ile Arg Gln Pro Ser Gly Lys Gly Leu Glu
                35                  40                  45

Trp Leu Ala His Ile Trp Trp Asp Gly Asp Glu Ser Tyr Asn Pro Ser
            50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Asn Arg Tyr Asp Pro Pro Trp Phe Val Asp Trp Gly Gln
                100                 105                 110

Gly Thr Leu Val Thr Val Ser Ser
                115                 120

<210> SEQ ID NO 5
<211> LENGTH: 107
<212> TYPE: PRT
<213> ORGANISM: Artificial
<220> FEATURE:
<223> OTHER INFORMATION: Synthesized- AB7 light chain variable region

<400> SEQUENCE: 5

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Ser Trp Tyr Gln Gln Lys Pro Gly Lys Ala Val Lys Leu Leu Ile
                35                  40                  45

Tyr Tyr Thr Ser Lys Leu His Ser Gly Val Pro Ser Arg Phe Ser Gly
            50                  55                  60

Ser Gly Ser Gly Thr Asp Tyr Thr Leu Thr Ile Ser Ser Leu Gln Gln
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys
                100                 105

<210> SEQ ID NO 6
<211> LENGTH: 120
<212> TYPE: PRT
<213> ORGANISM: Artificial
<220> FEATURE:
<223> OTHER INFORMATION: Synthesized- AB7 heavy chain variable region

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
                35                  40                  45

Trp Leu Ala His Ile Trp Trp Asp Gly Asp Glu Ser Tyr Asn Pro Ser
            50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95
```

```
Cys Ala Arg Asn Arg Tyr Asp Pro Pro Trp Phe Val Asp Trp Gly Gln
            100                 105                 110

Gly Thr Leu Val Thr Val Ser Ser
        115             120
```

METHODS FOR THE TREATMENT OF UVEITIS WITH IL-1β BINDING ANTIBODIES

RELATED APPLICATIONS

This application claims benefit of U.S. Application Ser. No. 13/102,768, filed May 6, 2011, issued as U.S. Pat. No. 8,551,487, and U.S. Provisional Application Nos. 61/444,638, filed Feb. 18, 2011; 61/334,125, filed May 12, 2010; and 61/332,658 filed May 7, 2010, the disclosures of which are herein incorporated by reference in their entirety.

FIELD OF INVENTION

The present disclosure relates to methods and materials for treating or preventing uveitis in a subject, including treatment refractory uveitis.

BACKGROUND OF THE INVENTION

Uveitis generally refers to intraocular inflammation and may, for example, affect the anterior portion of the uvea and/or the posterior portion of the uvea. Uveitis is a prevalent cause of visual impairment in many countries. The anterior portion of the uvea includes the iris and ciliary body. The posterior portion of the uvea includes the choroid. In addition to providing most of the blood supply of the intraocular structures, the uveal coat acts as a conduit for immune cells, particularly lymphocytes, to enter the eye. Consequently, it is directly involved in many intraocular inflammatory processes.

The international Uveitis Study Group classifies uveitis in terms of the eye(s) involved (i.e., unilateral or bilateral), course (i.e., acute, lasting less than 12 weeks, or chronic, lasting more than 12 weeks), and anatomical location in the eye (Bloch-Michel et al., *Am J Ophthalmol.*, 103:234-235, 1987). Further standardization of the characterization and nomenclature of uveitis is provided by the SUN working group (Jabs, et al., *Am J Ophtalmol.*, 140:509-516, 2005). Anterior uveitis includes, for example, iritis, anterior eyelids, and iridocyclitis involving the iris and/or pars plicata (anterior ciliary body). Intermediate uveitis includes, for example, pars planitis, posterior cyclitis, hyalitis, and basal retinochoroiditis, referring to inflammation of the pars plana (posterior ciliary body) and/or adjacent peripheral retina. Posterior uveitis includes focal, multifocal, or diffuse choroiditis; retinitis; neuroretinitis, retinochoroiditis; and chorioretinitis; the latter 2 terms indicate which tissue appears primarily involved. Panuveitis refers to inflammation that involves both the anterior and posterior segments. Uveitis may be further classified on the presence or absence of granulomatous inflammation, marked by "mutton fat" keratic precipitates, iris nodules, and/or choroidal granulomas.

Estimates indicate that uveitis may account for about 10% of the visual handicaps in the western world (Nussenblatt, *Int Ophthalmol.*, 14:303-308, 1990) and up to 15% of all cases of total blindness in the United States (Rothova el al., *Br J Ophthalmol.*, 80:332-436, 1996). Legal blindness develops in at least one eye in 22% of all uveitis patients and in about 23% of all who require intraocular surgery. In addition, visual acuity loss to worse than 6/18 in at least one eye occurs in 35% of patients with uveitis, mainly as a result of persistent macular edema (Rothova et al., ibid). The ocular complications of uveitis are usually involved in the decrease in visual acuity.

IL-1β is a proinflammatory cytokine secreted by a number of different ceil types including monocytes and macrophages. When released as part of art inflammatory reaction, IL-1β produces a range of biological effects, mainly mediated through induction of other inflammatory mediators such as corticotropin, platelet factor-4, prostaglandin E2 (PGE2), IL-6, and IL-8. IL-1β induces both local and systemic inflammatory effects through the activation of the IL-1 receptor found on almost all cell types. The interleukin-1 (IL-1) family of cytokines has been implicated in a number of disease states. IL-1 family members include IL-1α, IL-1β, and IL-1Ra. Although related by their ability to bind to IL-1 receptors (IL-1R1 and IL-1R2), each of these cytokines is different, being expressed by a different gene and having a different primary amino acid sequence. Furthermore, the physiological activities of these cytokines can he distinguished from each other.

Effective treatment of uveitis, including an acute uveitis exacerbation (e.g., uveitis flare, uveitis attack), with a complete resolution of inflammatory findings, is important for a better visual outcome. The longer a uveitis exacerbation goes unresolved, the greater are the chances of more severe sequela, incomplete resolution, and/or loss of vision. There remains a need for effective methods of treating and preventing uveitis. Including treatment of refractory uveitis and prevention of uveitis exacerbations including in at risk subjects.

SUMMARY OF THE INVENTION

The present disclosure relates to materials and methods for inhibiting (e.g., treating or preventing) uveitis in a subject, comprising administering to the subject an effective amount of anti-IL-1β antibody or binding fragment thereof. Surprisingly, the methods disclosed herein provide an effective means for inhibiting (e.g., treating or preventing) treatment refractory (e.g., treatment resistant) uveitis, with or without the use of additional pharmaceutical compositions, such as for example a non-steroid immunosuppressant, a non-steroid anti-inflammatory and/or a steroid. Such materials and methods may be used to treat a mammalian (e.g., human) subject suffering from uveitis disease (e.g., treatment refractory uveitis) or to prevent occurrence or reduce the frequency and/or severity of same in an at risk subject.

The present disclosure provides a method of inhibiting uveitis in a subject, the method comprising administering to the subject an effective amount of anti-IL-1β antibody or binding, fragment thereof, wherein the uveitis is treatment refractory (e.g., treatment resistant) uveitis. In some embodiments, the method of inhibiting uveitis in a subject is a method of preventing uveitis in the subject. In some embodiments, the method of inhibiting uveitis in a subject is a method of treating uveitis in the subject.

In some embodiments of each or any of the aforementioned methods, inhibiting uveitis in a subject is inhibiting an acute uveitis exacerbation.

In some embodiments of each or any of the aforementioned methods, inhibiting uveitis in a subject increases in the interval between acute uveitis exacerbations.

In some embodiments of each or any of the aforementioned methods, inhibiting uveitis in a subject decreases the frequency of acute uveitis exacerbations.

In some embodiments of each or any of the aforementioned methods, inhibiting uveitis in a subject decreases the likelihood of experiencing an acute uveitis exacerbation.

In some embodiments of each or any of the aforementioned methods, inhibiting uveitis in a subject prevents an acute uveitis exacerbation.

In some embodiments of each or any of the aforementioned methods, inhibiting uveitis in a subject treats an acute uveitis exacerbation. In some embodiments of each or any of the aforementioned methods, inhibiting uveitis in a subject decreases the severity of an acute uveitis exacerbation.

In some embodiments of each or any of the aforementioned methods, the treatment refractory uveitis is uveitis that is refractory to treatment with a pharmaceutical composition comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone, methylprenisolone, prednisolone, a cortisol, an andrenocorticotrophic hormone and a glucocorticoid (e.g., dexamethasone).

In some embodiments of each or any of the aforementioned methods, the subject is receiving concurrently for the inhibition of said uveitis at least one (e.g., one or two) pharmaceutical compositions comprising a non-steroid immunosuppressant, a non-steroid anti-inflammatory or a steroid. In some embodiments, the subject is receiving concurrently for the inhibition of said uveitis one pharmaceutical composition comprising a non-steroid immunosuppressant, a non-steroid anti-inflammatory or a steroid.

In some embodiments of each or any of the aforementioned methods, the subject is not receiving concurrently for the inhibition of said uveitis a pharmaceutical composition selected from the group consisting of a pharmaceutical composition comprising a non-steroid immunosuppressant, a pharmaceutical composition comprising a non-steroid anti-inflammatory and a pharmaceutical composition comprising a steroid. In some embodiments, the subject is not receiving concurrently for the treatment or prevention of said uveitis a pharmaceutical composition comprising a non-steroid immunosuppressant. In some embodiments, the subject is not receiving concurrently for the treatment or prevention of said uveitis a pharmaceutical composition comprising a non-steroid anti-inflammatory.

In some embodiments of each or any of the aforementioned methods, the subject has received prior treatment for uveitis with one or more pharmaceutical compositions comprising a non-steroid immunosuppressant, a non-steroid anti-inflammatory or a steroid. In some embodiments, the subject had an adverse reaction or hypersensitivity to said prior treatment of uveitis with one or more pharmaceutical compositions comprising a non-steroid immunosuppressant, a non-steroid anti-inflammatory or a steroid. In some embodiments, the subject failed said prior treatment of uveitis with one or more pharmaceutical compositions comprising a non-steroid immunosuppressant, a non-steroid anti-inflammatory or a steroid.

In some embodiments of each or any of the aforementioned methods, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate). X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone, methylprenisolone, prednisolone, a cortisol, an andrenocorticotrophic hormone and a glucocorticoid (e.g., dexamethasone).

In some embodiments of each or any of the aforementioned methods, the subject is receiving concurrently for the treatment or prevention of said uveitis at least one pharmaceutical composition comprising a non-steroid immunosuppressant, a non-steroid anti-inflammatory or a steroid, and wherein said method provides a reduction in the dosage of said at least one pharmaceutical composition. In some embodiments, the reduction in the dosage is a reduction in the dose of said at least one pharmaceutical composition, as compared to the dose prior to administering the anti-IL-1β antibody or binding fragment thereof. In some embodiments, the reduction in the dosage is a reduction in the frequency of doses of said at least one pharmaceutical composition, as compared to the frequency of doses prior to administering the anti-IL-1β antibody or binding fragment thereof. In some embodiments, the dosage of a pharmaceutical composition comprising a non-steroid immunosuppressant is reduced. In some embodiments, the non-steroid immunosuppressant is a DNA synthesis inhibitor, a cyclosporine, mycophenolate or a colchicine. In some embodiments, the DNA synthesis inhibitor is azathioprine or methotrexate. In some embodiments, the dosage of a pharmaceutical composition comprising a steroid is reduced. In some embodiments, the steroid is a steroid hormone selected from the group consisting of prednisone, prednisolone, methylprednisolone, a cortisol, an andrenocorticotrophic hormone and a glucocorticoid.

In some embodiments of each or any of the aforementioned methods, the method is a method of inhibiting an acute uveitis exacerbation in a subject diagnosed with uveitis, and wherein the acute uveitis exacerbation has a severity grade of at least a 2 step increase in intraocular inflammation according to SUN criteria.

The present disclosure provides a method of treating uveitis in a subject, the method comprising administering to the subject an effective amount of anti-IL-1β antibody or binding fragment thereof, wherein the uveitis is treatment refractory (e.g., treatment resistant) uveitis. In some embodiments, the treatment refractory uveitis is uveitis that is refractory to treatment with a pharmaceutical composition comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid.

The present disclosure also provides a method of treating or preventing uveitis in a subject, the method comprising administering to the subject an effective amount of anti-IL-1β antibody or binding fragment thereof, wherein the subject is receiving concurrently for the treatment or prevention of said uveitis at least one (e.g., one or two) pharmaceutical compositions comprising a non-steroid immunosuppressant, a non-steroid anti-inflammatory or a steroid. In some embodiments, the subject is receiving concurrently for the treatment or prevention said uveitis one pharmaceutical composition comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid.

The present disclosure also provides a method of treating or preventing uveitis in a subject, the method comprising administering to the subject an effective amount of anti-IL-1β antibody or binding fragment thereof, wherein the subject is receiving concurrently for the treatment or prevention of said uveitis a pharmaceutical composition comprising an interferon (e.g., IFN-α)

The present disclosure also provides a method of treating or preventing uveitis in a subject, the method comprising administering to the subject an effective amount of anti-IL-1β antibody or binding fragment thereof, wherein the uveitis is treatment refractory (e.g., treatment resistant) uveitis and wherein the subject is hot receiving concurrently for the treatment or prevention of said uveitis a pharmaceutical composition selected from the group consisting of a pharmaceutical composition comprising a non-steroid immunosuppressant, a pharmaceutical composition comprising a non-steroid anti-inflammatory and a pharmaceutical composition comprising a steroid. In some embodiments, the subject is not receiving concurrently for the treatment or prevention of said uveitis a pharmaceutical composition comprising a non-steroid immunosuppressant. In some embodiments, the subject is not receiving concurrently for the treatment or prevention of said uveitis a pharmaceutical composition comprising a non-steroid anti-inflammatory. In some embodiments, the subject is not receiving concurrently for the treatment or prevention of said uveitis a pharmaceutical composition comprising a steroid. In some embodiments, the subject is not receiving concurrently for the treatment or prevention of said uveitis a pharmaceutical composition comprising a non steroid immunosuppressant and a pharmaceutical composition comprising a non-steroid anti-inflammatory. In some embodiments, the subject is not receiving concurrently for the treatment or prevention of said uveitis a pharmaceutical composition comprising a non steroid immunosuppressant and a pharmaceutical composition comprising a steroid. In some embodiments, the subject is not receiving concurrently for the treatment or prevention of said uveitis a pharmaceutical composition comprising a non-steroid anti-inflammatory and a pharmaceutical composition comprising a steroid. In some embodiments, the subject is not receiving concurrently for the treatment or prevention of said uveitis any of a pharmaceutical composition comprising a non steroid immunosuppressant, a pharmaceutical composition comprising a non-steroid anti-inflammatory and a pharmaceutical composition: comprising a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid.

In some embodiments of each or any of the aforementioned methods, the treatment refractory uveitis is uveitis that is refractory to treatment with a pharmaceutical composition selected from the group consisting of a pharmaceutical composition comprising a non-steroid immunosuppressant, a pharmaceutical composition comprising a non-steroid anti-inflammatory and a pharmaceutical composition comprising a steroid. In some embodiments, the treatment refractory uveitis is uveitis that is refractory to treatment with a pharmaceutical composition comprising a non-steroid immunosuppressant. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the treatment refractory uveitis is uveitis that is refractory to treatment with a pharmaceutical composition comprising a non-steroid anti-inflammatory. In some embodiment, the non-steroid anti-inflammatory is a TNF inhibitors an IL-6 inhibitor or an IL-17 inhibitor. In some embodiments, the treatment refractory uveitis is uveitis that is refractory to treatment with a pharmaceutical composition comprising a steroid. In some embodiments, the steroid is a steroid hormone selected from the group consisting of prednisone (e.g., methylprenisolone, prednisolone), cortisol, andrenocorticotrophic hormone and a glucocorticoid.

The present disclosure also provides a method of Inhibiting an acute uveitis exacerbation (e.g., uveitis flare) in a subject, the method comprising administering to the subject an effective amount of anti-IL-1β antibody or binding fragment thereof, wherein the subject has received prior treatment for uveitis with one or more pharmaceutical compositions comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting prednisone (e.g., methylprenisolone, prednisolone), cortisol, andrenocorticotrophic hormone and a glucocorticoid. In some embodiments, the subject had an adverse reaction or hypersensitivity to said prior treatment of uveitis with one or more pharmaceutical compositions comprising a non-steroid immunosuppressant, a non-steroid anti-inflammatory or a steroid. In some embodiments, the subject failed said prior treatment of uveitis with one or more pharmaceutical compositions comprising a non-steroid immunosuppressant, a non-steroid anti-inflammatory or a steroid. In some embodiments, the subject partially responded to said prior treatment of uveitis with one or more pharmaceutical compositions comprising a non-steroid immunosuppressant, a non-steroid anti-inflammatory or a steroid. In some embodiments, the acute uveitis exacerbation has a severity grade of at least a 2 step increase in intraocular inflammation according to SUN criteria.

The disclosure also provides a method of inhibiting an acute uveitis exacerbation (e.g., uveitis flare) in a subject, the method comprising administering to the subject an effective amount of anti-IL-1β antibody or binding fragment thereof wherein the subject is receiving concurrent treatment for said uveitis with at least one (e.g., one or two) pharmaceutical compositions comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid. In some embodiments, the acute uveitis exacerbation has a severity grade of at least a 2 step increase in intraocular inflammation according to SUN criteria.

The disclosure also provides a method of inhibiting an acute uveitis exacerbation, in a subject, the method comprising administering to the subject an effective amount of anti-IL-1β antibody or binding fragment thereof, wherein the subject Is receiving concurrently for the treatment or prevention of said uveitis a pharmaceutical composition comprising an interferon (e.g., IFN-α)

In some embodiments of each or any of the aforementioned methods, said inhibiting an acute uveitis exacerbation is an increase in the interval between acute uveitis exacerbations (e.g., between two or more acute uveitis exacerbations). In some embodiments, said inhibiting an acute uveitis exacerbation is a decrease In the frequency of acute uveitis exacerbations. In some embodiments, said inhibiting an acute uveitis exacerbation is a decrease in the likelihood of experiencing an acute uveitis exacerbation. In some embodiments, said inhibiting an acute uveitis exacerbation is preventing an acute uveitis exacerbation. In some embodiments, said inhibiting an acute uveitis exacerbation is treating an acute uveitis exacerbation. In some embodiments, said inhibiting an acute uveitis exacerbation is decreasing the severity of an acute uveitis exacerbation.

The disclosure also provides a method of treating or preventing uveitis in a subject, the method comprising administering to the subject an effective amount of anti-IL-1β antibody or binding fragment thereof, wherein the subject is receiving concurrently for the treatment or prevention of said uveitis at least one pharmaceutical composition comprising a non-steroid immunosuppressant, a non-steroid anti-inflammatory or a steroid, and wherein said method provides a reduction (e.g., tapering) in the dosage of said at least one pharmaceutical composition. In some embodiments, the reduction in dosage is a reduction in the dose of said at least one pharmaceutical composition, as compared to the dose prior to administering the anti-IL-1β antibody or binding fragment thereof. In some embodiments, the reduction in dosage is a reduction in the frequency of doses of said at least one pharmaceutical composition, as compared to the frequency of doses prior to administering the anti-IL-1β antibody or binding fragment thereof. In some embodiments, the reduction in dosage is a redaction in cumulative exposure to said at least one pharmaceutical composition over a period of time (e.g., days, weeks, months) after administering the anti-IL-1β antibody or binding fragment thereof, as compared to the cumulative exposure over a similar period of time prior to administering the anti-IL-1β antibody or binding fragment thereof. In some embodiments, reduction in cumulative exposure is a reduction in area under the curve (e.g., AUG). In some embodiments, the reduction in area under the curve is shown by reduced average blood concentration of the at least one pharmaceutical composition over a time-adjusted integrated average (e.g., for a time vs. drug dose). In some embodiments, the dosage of a pharmaceutical composition comprising a steroid is reduced. In some embodiments, the dosage of a pharmaceutical composition comprising a non-steroid immunosuppressant is reduced. In some embodiments, the dosage of a pharmaceutical composition comprising a non-steroid anti-inflammatory is reduced. In some embodiments, the dosage of at least two pharmaceutical compositions comprising a steroid, non-steroid immunosuppressant or a non-steroid anti-inflammatory is reduced. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid (e.g., dexamethasone).

The disclosure also provides a method of inhibiting an acute uveitis exacerbation (e.g., uveitis flare) in a subject diagnosed with uveitis, the method comprising administering to the subject an effective amount of anti-IL-1β antibody or binding fragment thereof, wherein the uveitis is treatment refractory (e.g., treatment resistant) uveitis and wherein the acute uveitis exacerbation has a severity grade of at least a 2 step increase in intraocular inflammation according to the SUN criteria.

The disclosure also provides a method of inhibiting an acute uveitis exacerbation (e.g., uveitis flare) in a subject diagnosed with uveitis, the method comprising administering to the subject an effective amount of anti-IL-1β antibody or binding fragment thereof, wherein the uveitis is treatment refractory (e.g., treatment, resistant) uveitis and wherein the acute uveitis exacerbation has a new area of retinitis.

In some embodiments of each or any of the aforementioned methods, the subject is a subject at risk for an acute uveitis exacerbation.

The disclosure also provides a method of inhibiting (e.g., treating, preventing) uveitis in a subject, the method comprising administering to the subject an anti-IL-1β antibody or binding fragment thereof in a dose amount and frequency sufficient to maintain a systemic trough serum concentration of at least about 0.5 µg/mL, at least about 1.0 µg/mL, at least about 1.5 µg/mL, at least about 2.0 µg/mL, at least about 3.0 µg/mL, at least about 4.0 µg/mL or at least about 5.0 µg/mL of anti-IL-1β antibody or binding fragment thereof. In some embodiments, the anti-IL-1β antibody or binding fragment thereof is administered in a dose amount and frequency sufficient to maintain a systemic trough serum concentration between about 0.5 µg/mL and about 5 µg/mL, between about 1 µg/mL and 5 µg/mL or between about 2 µg/mL and 5 µg/mL.

The disclosure also provides a method of treating uveitis in a subject, the method comprising; 1) diagnosing uveitis in the subject, and 2) administering to the subject of step 1) an effective amount of anti-IL-1β antibody or binding fragment thereof, wherein said method results in an improvement in anterior uveitis or posterior uveitis. In some embodiments, the method results in an improvement in both anterior uveitis and posterior uveitis. In some embodiments, the subject diagnosed with uveitis is a subject diagnosed with panuveitis. In some embodiments, the method further results in an improvement in intermediate uveitis.

The disclosure also provides a method of treating uveitis in a subject, the method comprising: 1) diagnosing uveitis in the subject, and 2) administering to the subject of step 1) an effective amount of anti-IL-1β antibody or binding fragment thereof wherein said method results in an improvement in at least one or two parameters (e.g., at least three parameters, at least four parameters, at least five parameters) selected from visual acuity, vitreous haze, anterior chamber cell score, macular edema, laser flare cell count (e.g., flare score), subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, vascular leakage (e.g., fundus fluorescein angiography leakage score, dual fluorescein angiography and indocyanine green angiography score), optic disc hyperfluorescence, disc margin staining, optic disc leakage, cystic pooling, posterior pole arcades, retinal capillary nonperfusion, macular ischemia, pinpoint leaks, retinal staining, iritis, iridocyclitis, anterior cyclitis, pars planitis, posterior cyclitis, focal choroiditis, multifocal choroiditis, diffuse choroiditis, chorioretinitis, retinochoroiditis, retinitis, neuroretinitis, retinal dysfunction and elevated intraocular pressure.

In some embodiments of each or any of the aforementioned methods, the method results in an improvement in at least one or two parameters (e.g., at least three parameters, at least four parameters, at least five parameters) selected from visual acuity, vitreous haze, anterior chamber cell score, macular edema, laser flare cell count (e.g., flare score), subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, fundus fluorescein angiography leakage score, optic disc hyperfluorescence, disc margin staining, optic disc leakage, cystic pooling, posterior pole arcades, retinal capillary nonperfusion, macular ischemia, pinpoint leaks, retinal staining, iritis, iridocyclitis, anterior cyclitis, pars planitis, posterior eyelids, focal choroiditis, multifocal choroiditis, diffuse choroiditis, chorioretinitis, retinochoroiditis, retinitis and neuroretinitis. In some embodiments, the method results in an improvement in Ben Ezra score.

In some embodiments of each or any of the aforementioned methods, the method results in an improvement in at least one or two parameters (e.g., at least three parameters, at least four parameters, at least five parameters) selected from visual acuity, vitreous haze, anterior chamber cell score, macular edema, laser flare cell count (e.g., flare score), subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, fundus fluorescein angiography leakage score, optic disc hyperfluorescence, disc margin staining, optic disc leakage, cystic pooling, posterior pole arcades, retinal capillary nonperfusion, macular ischemia, pinpoint leaks and retinal staining. In some embodiments, the method results in an improvement in Ben Ezra score.

In some embodiments of each or any of the aforementioned methods, the method results in an improvement in at least one or two parameters at least three parameters, at least four parameters, at least five parameters) selected from visual acuity, vitreous haze, laser flare cell count (e.g., flare score), retinal infiltrates, retinal vasculitis and optic disk hyperfluorescence. In some embodiments, the method results in an improvement in Ben Ezra score.

In some embodiments of each or any of the aforementioned methods, the method results in an improvement in at least one or two parameters (e.g., at least three parameters, at least four parameters) selected from visual acuity, vitreous haze, laser flare cell count (e.g., flare score) and retinal vasculitis. In some embodiments, the method results in an improvement in at least two parameters selected from visual acuity, vitreous haze, laser flare cell count (e.g., flare score) and retinal vasculitis. For example, an improvement in one parameter may be an improvement in visual acuity, vitreous haze, laser flare cell count (e.g., flare score) or retinal vasculitis. For example, an improvement in two parameters may be an improvement in two of visual acuity, vitreous base, laser flare cell count (e.g., flare score) or retinal, vasculitis. In some embodiments of each or any of the aforementioned methods, the method results in an improvement in Ben Ezra score.

The disclosure also provides a method of treating uveitis in a subject, the method comprising: 1) diagnosing uveitis in the subject, and 2) administering to the subject of step 1) an effective amount of anti-IL-1β antibody or binding fragment thereof, wherein said method results in an improvement in at least one of visual acuity, vitreous base, laser flare cell count (e.g., flare score) and retinal vasculitis.

In some embodiments of each or any of the aforementioned methods, the uveitis in non-infectious uveitis.

In some embodiments of each or any of the aforementioned methods, the subject has been diagnosed with a disease or condition selected from Behçet's disease, spondyloarthritides (e.g., ankylosing spondylitis, reactive arthritis), psoriatic arthritis, psoriasis, inflammatory bowel disease, ulcerative colitis, sarcoidosis, tubulointerstitial nephritis and uveitis (TINU) syndrome, rheumatoid arthritis, Kawasaki disease, Sjögren's syndrome, systemic lupus erythematosus, polyarteritis, Reiter disease, Wegener's granulomatosis, Vogt-Koyanagi-Harada syndrome, systemic juvenile idiopathic arthritis and granulomatous angiitis.

In some embodiments of each or any of the aforementioned methods, the subject has been diagnosed with cytomegalovirus infection, toxoplasmosis, syphilis, tuberculosis, cat scratch disease, Lyme disease, West Nile virus infection, herpes simplex virus infection, human immunodeficiency virus infection, fungal infection or varicella-zoster infection.

In some embodiments of each or any of the aforementioned methods, the subject has been diagnosed with a disease or condition selected from pars planitis, multiple sclerosis, sympathetic ophthalmia, birdshot choroidopathy, immune recovery uveitis (e.g., immune reconstitution inflammatory syndrome), lymphoma and idiopathic uveitis.

The present disclosure also provides a method of treating Behçet's disease in a subject, the method comprising administering to the subject an effective amount of anti-IL-1β antibody or binding fragment thereof, wherein the subject has been diagnosed with uveitis and said uveitis is treatment refractory (e.g., treatment resistant) uveitis. In some embodiments, the treatment refractory uveitis is uveitis that is refractory to treatment with a pharmaceutical composition comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate). X-ray therapy, chlorambucil, or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid.

The disclosure also provides a method of treating Behçet's disease in a subject the method comprising administering to the subject an effective amount of anti-IL-1β antibody or binding fragment thereof, said method further comprising treating an acute uveitis exacerbation (e.g., uveitis flare), wherein the subject has been diagnosed with uveitis and said uveitis is treatment refractory uveitis, and wherein the subject is receiving concurrent treatment for said acute uveitis exacerbation with one or two pharmaceutical compositions comprising a non-steroid immunosuppressant, a non-steroid anti-inflammatory or a steroid. In some embodiments, the non-steroid immunosuppressant is a DNA synthesis inhibitor, a cyclosporine, a mycophenolate or a colchicine. In some embodiments, the DNA synthesis inhibitor is azathioprine, an alkylating agent, an anti-metabolite (e.g., methotrexate), X-ray therapy, chlorambucil or cyclophosphamide. In some embodiments, the non-steroid anti-inflammatory is a TNF inhibitor, an IL-6 inhibitor or an IL-17 inhibitor. In some embodiments, the steroid is a steroid hormone selected from the group consisting of prednisone (e.g., methylprenisolone, prednisolone), cortisol, andrenocorticotrophic hormone and a glucocorticoid. In some embodiments, the acute uveitis exacerbation has a severity grade of at least a 2 step increase in intraocular inflammation according to SUN criteria.

In some embodiments of each or any of the aforementioned methods, the method results in an improvement in anterior uveitis or posterior uveitis. In some embodiments, the method results in an improvement in both anterior uveitis and posterior uveitis.

In some embodiments of each or any of the aforementioned methods, the method results in an improvement in at least one or two parameters (e.g., at least three parameters, at least four parameters, at least five parameters) selected from visual acuity, vitreous haze, anterior chamber cell score, macular edema, laser flare cell count (e.g., flare score), subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, vascular leakage (e.g., fundus fluorescein angiography leakage score, dual fluorescein angiography and indocyanine green angiography score), optic disc hyperfluorescence, disc margin staining, optic disc leakage, cystic pooling, posterior pole arcades, retinal capillary nonperfusion, macular ischemia, pinpoint leaks, retinal staining, iritis, iridocyclitis, anterior eyelids, pars planitis, posterior cyclitis, focal choroiditis, multifocal choroiditis, diffuse choroiditis, chorioretinitis, retinochoroiditis, retinitis, neuroretinitis, retinal dysfunction and elevated intraocular pressure.

In some embodiments of each or any of the aforementioned methods, the method results in an improvement in at least one or two parameters (e.g., at least three parameters, at least four parameters, at least five parameters) selected from visual acuity, vitreous base, anterior chamber cell score, macular edema, laser flare cell count (e.g., flare score), subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, fundus fluorescein angiography leakage score, optic disc hyperfluorescence, disc margin staining, optic disc leakage, cystic pooling, posterior pole arcades, retinal capillary nonperfusion, macular ischemia, pinpoint leaks, retinal staining, iritis, iridocyclitis, anterior cyclitis, pars planitis, posterior cyclitis, focal choroiditis, multifocal choroiditis, diffuse choroiditis, chorioretinitis, retinochoroiditis, retinitis and neuroretinitis.

In some embodiments of each or any of the aforementioned methods, the method results in an improvement in at least one or two parameters (e.g., at least three parameters, at least four parameters, at least five parameters) selected from visual acuity, vitreous haze, anterior chamber cell score, macular edema, laser flare cell count (e.g., flare score), subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, fundus fluorescein angiography leakage score, optic disc hyperfluorescence, disc margin staining, optic disc leakage, cystic pooling, posterior pole arcades, retinal capillary nonperfusion, macular ischemia, pinpoint leaks and retinal staining.

In some embodiments of each or any of the aforementioned methods, the method results in an improvement in at least one or two parameters (e.g., at least three parameters, at least four parameters, at least five parameters) selected from visual acuity, vitreous haze, laser flare cell count (e.g., flare score), retinal infiltrates, retinal vasculitis and optic disk hyperfluorescence.

In some embodiments of each or any of the aforementioned methods, the method results in an improvement in at least one or two parameters (e.g., at least three parameters, at least four parameters) selected from visual acuity, vitreous haze, laser flare cell count (e.g., flare score) and retinal vasculitis. In some embodiments, the method results in an improvement in at least two parameters selected from visual acuity, vitreous haze, laser flare cell count (e.g., flare score) and retinal vasculitis. For example, an improvement in one parameter may be an improvement in visual acuity, vitreous haze, laser flare cell count (e.g., flare score) or retinal vasculitis, for example, an improvement in two parameters may be an improvement in two of visual acuity, vitreous haze, laser flare cell count (e.g., flare score) or retinal vasculitis.

In some embodiments each or any of the aforementioned methods, the method results in an improvement in Ben Ezra score.

In some embodiments of each or any of the aforementioned methods, the antibody or antibody fragment binds to human IL-1β with a dissociation constant of about 1 nM or less. In some embodiments, the antibody or antibody fragment binds to human IL-1β with a dissociation constant of about 250 pM or less. In some embodiments, the antibody or antibody fragment binds to human IL-1β with a dissociation constant of about 50 pM or less. in some embodiments, the antibody or antibody fragment binds to human IL-1β with a dissociation constant of about 10 pM or less. In some embodiments, the antibody or antibody fragment binds to human IL-1β with a dissociation constant of about 1 pM or less. In some embodiments, the antibody or antibody fragment binds to human IL-1β with a dissociation constant of about 0.3 pM or less.

In some embodiments of each or any of the aforementioned methods, the anti-IL-1β antibody or binding fragment thereof is a neutralizing antibody.

In some embodiments of each or any of the aforementioned methods, the anti-IL-1β antibody or binding fragment thereof binds to an IL-1β epitope such that the bound antibody or fragment substantially permits the binding of IL-1β to IL-1 receptor I (IL-1R1).

In some embodiments of each or any of the aforementioned methods, the anti-IL-1β antibody or binding fragment thereof does not detectably bind to IL-1α, IL-1R or IL-1Ra.

In some embodiments of each or any of the aforementioned methods, the anti-IL-1β antibody or binding fragment, thereof competes with the binding of an antibody having the light chain, variable region of SEQ ID NO:5 and the heavy chain variable region of SEQ ID NO:6.

In some embodiments of each or any of the aforementioned methods, the anti-IL-1β antibody or binding fragment thereof binds to an epitope of IL-1β that is substantially the same as the epitope bound by an antibody having the light chain variable region of SEQ ID NO:5 and the heavy chain variable region of SEQ ID NO:6.

In some embodiments of each or any of the aforementioned methods, the anti-IL-1β antibody or binding fragment thereof binds to an epitope incorporating Glu64 of IL-1β.

In some embodiments of each or any of the aforementioned methods, the antibody or antibody fragment binds to amino acids 1-34 of the N terminus of IL-1β.

In some embodiments, each or any of the anti-IL-1β antibody or binding fragment thereof is Human Engineered or humanized.

In some embodiments, each or any of the anti-IL-1β antibody or binding fragment thereof is human.

In some embodiments of each or any of the aforementioned methods, the anti-IL-1β antibody or binding fragment thereof is administered in one or more doses of about 3 mg/kg or less of antibody or fragment. In some embodiments, the antibody or antibody fragment is administered in one or more doses of about 1 mg/kg or less of antibody or fragment. In some embodiments, the antibody or antibody fragment is administered in one or more doses of about 0.3 mg/kg or less of antibody or fragment. In some embodiments, the antibody or antibody fragment is administered in one or more doses of about 0.1 mg/kg or less of antibody or fragment. In some embodiments, the antibody or antibody fragment is administered in one or more doses of about 0.03 mg/kg or less of antibody or fragment. In some embodiments, the antibody or antibody fragment is administered in one or more doses of about 0.01 mg/kg or less of antibody or fragment. In some embodiments, the one or more doses are at least about 0.01 mg/kg of antibody or fragment.

In some embodiments of each or any of the aforementioned methods, the anti-IL-1β antibody or binding fragment thereof is administered as a fixed dose, independent of a dose per subject weight ratio. In some embodiments, the antibody or fragment is administered in one or more doses of 500 mg or less of antibody or fragment. In some embodiments, the antibody or fragment is administered in one or more doses of 250 mg or less of antibody or fragment. In some embodiments, the antibody or fragment is administered in one or more doses of 100 mg or less of antibody or fragment. In some embodiments, the antibody or fragment is administered in one or more doses of 50 mg or less of antibody or fragment. In some embodiments, the antibody or fragment is administered in one or more doses of 25 mg or less of antibody or fragment, in some embodiments, the antibody or fragment is administered in one or more doses of 10 mg or less of antibody or fragment. In some embodiments, the antibody or fragment is administered in one or more doses of 1.0 mg or less of antibody or fragment. In some embodiments, the antibody or fragment is administered in one or more doses of at least 1.0 mg of antibody or fragment. In some embodiments, the antibody or fragment is administered in one or more doses of at least 10 mg of antibody or fragment. In some embodiments, the antibody or fragment is administered in one or more doses of about 5 mg to about 150 mg of antibody or fragment, in some embodiments, the antibody or fragment is administered in one or more doses of about 10 mg to about 75 mg of antibody or fragment (e.g., 20 mg, 30 mg, 40 mg, 50 mg, 60 mg or 70 mg). In some embodiments, the antibody or fragment is administered in one or more doses of about 20 mg to about 50 mg of antibody or fragment. In some embodiments, the antibody or fragment is administered in one or more doses of about 30 mg of antibody or fragment.

In some embodiments of each or any of the aforementioned methods, administration of an initial dose of the antibody or antibody fragment is followed by the administration of one or more subsequent doses. In some embodiments, administration of an initial dose of the antibody or antibody fragment is followed by the administration of one or more subsequent doses, and wherein said one or more subsequent doses are in an amount that is approximately the same or less than the initial dose. In some embodiments, administration of an initial dose of the antibody or antibody fragment is followed by the administration of one or more subsequent doses, and wherein said one or more subsequent doses are in an amount that is approximately 10% less than an initial dose, 20% less than the initial dose, 30% less than the initial dose, 40% less than the initial dose, 50% less than the initial dose, 60% less than the initial dose, 70% less than the initial dose, 80% less than the initial dose, or 90% less than the initial dose. For example, when an initial dose of 40 mg is given, one or more subsequent doses may be 20% less (32 mg), 30% less (28 mg), 40% less (24 mg), 50% less (20 mg), 60% less (16 mg), etc. As another example, when an initial dose of 50 mg is given, one or more subsequent doses may be 20% less (40 mg), 30% less (35 mg), 40% less (30 mg), 50% less (25 mg), 60% (20 mg), etc. As yet another example, when an initial dose of 60 mg is given, one or more subsequent doses may be 20% less (48 mg), 30% less (42 mg), 40% less (36 mg), 50% less (30 mg), 60% (24 mg), etc. In some embodiments, administration of an initial dose of the antibody or antibody fragment is followed by the administration of one or more subsequent doses, and wherein at least one of the subsequent doses is in an amount that is more than the initial dose. In some embodiments, administration of an initial dose of the antibody or antibody fragment is followed by the administration of one or more subsequent doses, and wherein at least one of the subsequent doses is in an amount that is at least 10% more, 20% more, 30% more, 40% more 50% more, 75% more or 100% more than the initial dose. For example, when an initial dose of 20 mg is given, one or more subsequent doses may be 20% more (24 mg), 30% more (26 mg), 40% more (28 mg), 50% more (30 mg), 100% more (40 mg), etc. As another example, when an initial dose of 30 mg is given, one or more subsequent doses may be 20% more (36 mg), 30% more (39 mg), 40% more (42 mg), 50% more (45 mg), 100% more (60 mg), etc. As yet another example, when an initial dose of 40 mg is given, one or more subsequent doses may be 20% more (48 mg), 30% more (52 mg), 40% more (56 mg), 50% more (60mg), 100% more (80 mg), etc.

In some embodiments of each or any of the aforementioned methods, the anti-IL-1β antibody or binding fragment thereof is administered in a dose amount and frequency sufficient to maintain a systemic trough serum concentration of at least about 0.5 µg/mL, at least about 1.0 µg/mL, at least about 1.5 µg/mL, at least about 2.0 µg/mL, at least about 3.0 µg/mL, at least about 4.0 µg/mL or at least about 5.0 µg/mL of anti-IL-1β antibody or binding fragment thereof. In some embodiments, the anti-IL-1β antibody or binding fragment thereof is administered in a dose amount and frequency sufficient to maintain a systemic trough serum concentration between about 0.5 µg/mL and about 5 µg/mL between about 1 µg/mL and 5 µg/mL. or between about 2 µg/mL and 5 µg/mL. In some embodiments of each or any of the aforementioned methods, the anti-IL-1β antibody or binding fragment thereof has a lower IC$_{50}$ than an IL-1β receptor antagonist in a human whole blood IL-1β inhibition assay that measures IL-1β induced production of IL-8. In some embodiments, the IL-IL-1β receptor antagonist is anakinra.

The disclosure also provides for use of an anti-IL-1β antibody or binding fragment thereof which has a lower IC$_{50}$ than an IL-1β receptor antagonist in a human whole blood IL-1β inhibition assay that measures IL-1β induced production of IL-8, in the manufacture of a composition for use in the treatment of uveitis, wherein the uveitis is treatment refractory (e.g., treatment resistant) uveitis. In some embodiments, the IL-1β receptor antagonist is anakinra.

It is to be understood that where the present specification mentions methods of treatments making use of antibodies or binding fragments thereof with certain properties (such as Kd values or IC$_{50}$ values), this also means to embody the use of such antibodies or fragments thereof in the manufacture of a medicament for use in these methods. Further, the invention also encompasses antibodies or binding fragments thereof having these properties as well as pharmaceutical compositions comprising these antibodies or binding fragments thereof for use in the methods of treatment discussed hereinafter.

BRIEF DESCRIPTION OF THE DRAWINGS

FIG. 1 is a table showing seven subjects from the IL-1β antibody clinical trial, with information about, treatment medicines received prior to enrollment in the study.

FIG. 2 is a table showing clinical data for subject 1001 treated with an IL-1β antibody.

FIG. 3 is a table showing clinical data for subject 1002 treated with an IL-1β antibody, FIG. 4 is a table showing clinical data for subject 1003 treated with an IL-1β antibody, FIG. 5 is a table showing clinical data for subject 1004 treated with an IL-1β antibody.

FIG. 6 is a table showing clinical data for subject 1005 treated with an IL-1β antibody.

FIG. 7 is a table showing clinical data for subject 1006 treated with an IL-1β antibody.

FIG. 8 is a table showing clinical data for subject 1007 treated with an IL-1β antibody.

FIG. 9 is images showing resolution of a hypopyon following treatment with an IL-1β antibody.

FIG. 10 is Images showing resolution of vitreous haze following treatment with an IL-1β antibody.

DETAILED DESCRIPTION

Effective therapies for use in treating or preventing uveitis have remained an important medical need. The present disclosure provides methods and materials, and related articles of manufacture, for treating or preventing uveitis in a subject; including, treatment refractory (e.g., treatment resistant) uveitis, comprising administering to the subject an effective amount of anti-IL-1β antibody or binding fragment thereof. Such materials and methods may be used to replace or complement other pharmaceutical approaches as provided herein.

IL-1β is a pro-inflammatory cytokine secreted by a number of different cell types including monocytes and macrophages. When released as part of an inflammatory reaction, IL-1β produces a range of biological effects, mainly mediated through induction of other inflammatory mediators such as corticotrophin, platelet factor-4, prostaglandin E2 (PGE2), IL-6, and IL-8. IL-1β induces both local and systemic inflammatory effects through the activation of the IL-1 receptor found on almost all cell types.

The interleukin-1 (IL-1) family of cytokines has been implicated in several disease states such as rheumatoid arthritis (RA), osteoarthritis, Crohn's disease, ulcerative colitis (UC), septic shock, chronic obstructive, pulmonary disease (COPD), asthma, graft versus host disease, atherosclerosis, adult T-cell leukemia, multiple myeloma, multiple sclerosis, stroke, and Alzheimer's disease. IL-1 family members include IL-1α, IL-1β, and IL-1Ra. Although related by their ability to bind to IL-1 receptors (IL-1R1, IL-1R2), each of these cytokines is expressed by a different gene and has a different primary amino acid sequence. Furthermore, the physiological activities of these cytokines can he distinguished from each other.

Compounds that disrupt IL-1 receptor signaling have been investigated as therapeutic agents to treat IL-1 mediated diseases, such as for example some of the aforementioned diseases. These compounds Include recombinant IL-1Ra (Amgen Inc., Thousand Oaks, Calif.). IL-1 receptor "trap" peptide (Regeneron Inc., Tarrytown, N.Y.), as well as animal-derived IL-1β antibodies and recombinant IL-1β antibodies and fragments thereof.

As noted above, IL-1 receptor antagonist (IL-1Ra) polypeptide has been suggested for use in the treatment of gout (So et al., 2007, ibid; McGonagle et al., 2007, ibid), but there remains a need for effective means to treat gout, particularly those that do not require daily, repeated injections. An additional challenge for IL-1 receptor antagonist-based therapeutics is the need for such therapeutics to occupy a large number of receptors, which is a formidable task since these receptors are widely expressed on all cells except red blood cells (Dinarello, Curr. Opin. Pharmacol. 4:378-385, 2004). In most immune-mediated diseases, such as the diseases disclosed herein, the amount of IL-1β cytokine that is measurable in body fluids or associated with activated ceils is relatively low. Thus, a method of treatment and/or prevention that directly targets the IL-1β ligand is a superior strategy, particularly when administering an IL-1β antibody with high affinity.

The present invention provides methods and related compositions and articles of manufacture for the treatment and/or prevention, of gout in a subject (e.g., mammalian, human), using an antibody or fragment thereof specific for IL-1β.

As shown in Example 1 below, we have surprisingly found that such an antibody (e.g., with very high affinity) can be far more potent an Inhibitor of the IL-1 pathway than is IL-Ra (e.g., Kineret®), and provides an opportunity to achieve a therapeutic effect at a lower dose and/or with less frequent -administration than necessary for other drugs, such as recombinant IL-1Ra.

Such methods as described herein with an IL-1β antibody or fragment may include the treatment of a subject suffering from gout (e.g., acute gout, chronic gout, refractory gout). The methods also may include preventing the occurrence of gout (e.g., acute-gout, chronic gout, refractory gout) in an at risk subject.

Antibodies, Humanized Antibodies, and Human Engineered Antibodies

The IL-1 (e.g., IL-1β) binding antibodies of the present disclosure may be provided as polyclonal antibodies, monoclonal antibodies (mAbs), recombinant antibodies, chimeric antibodies, CDR-grafted antibodies, fully human antibodies, single chain antibodies, and/or bispecific antibodies, as well as fragments, including variants and derivatives thereof, provided by known techniques, including, but not limited to enzymatic cleavage, peptide synthesis or recombinant techniques.

Antibodies generally comprise two heavy chain polypeptides and two light chain polypeptides, though single domain antibodies having one heavy chain and one light chain, and heavy chain antibodies devoid of light chains are also contemplated. There are five types of heavy chains, called alpha, delta, epsilon, gamma and mu, based on the amino acid sequence of the heavy chain constant domain. These different types of heavy chains give rise to five classes of antibodies, IgA (including $IgA_1$ and $IgA_2$), IgD, IgE, IgG and IgM, respectively, including four subclasses of IgG, namely $IgG_1$, $IgG_2$, $IgG_3$ and $IgG_4$. There are also two types of light chains, called kappa (κ) or lambda (λ) based on the amino acid sequence of the constant domains. A full-length antibody includes a constant domain and a variable domain. The constant region need not be present in an antigen binding fragment of an antibody. Antigen binding fragments of an antibody disclosed herein can include Fab, Fab', F(ab')$_2$, and F(v) antibody fragments. As discussed in more detail below, IL-1β binding fragments encompass antibody fragments and antigen-binding polypeptides that will bind IL-1β.

Each of the heavy chain and light chain sequences of an antibody, or antigen binding fragment thereof, includes a variable region with three complementarity determining regions (CDRs) as well as non-CDR framework regions (FRs). The terms "heavy chain" and "light chain," as used herein, mean the heavy chain variable region and the light chain variable region, respectively, unless otherwise noted. Heavy chain CDRs are referred to herein as CDR-H1, CDR-H2, and CDR-H3. Light chain CDRs are referred to herein as CDR-L1, CDR-L2, and CDR-L3. Variable regions and CDRs In an antibody sequence can be identified (i) according to general rules that have been developed in the art or (ii) by aligning the sequences against a database of known variable regions. Methods for Identifying these regions are described in Kontermann and Dubel, eds., *Antibody Engineering*, Springer, New York, N.Y., 2001, and Dinarello et al., *Current Protocols in Immunology*, John Wiley and Sons Inc., Hoboken, N.J., 2000. Databases of antibody sequences are described in and can be accessed through "The Kabatman" database at bioinforg.uk/abs (maintained by A. C. Martin in the Department of Biochemistry & Molecular Biology University College London, London, England) and VBASE2 at vbase2.org, as described in Retter et al., *Nucl. Acids Res.*, 33(Database Issue): D671-D674 (2005). The "Kabatman" database web site also includes general rules of thumb for identifying CDRs. The term "CDR," as used herein, is as defined in Kabat et al., *Sequences of Immunological Interest*, 5th ed., U.S. Department of Health and Human Services, 1991, unless otherwise indicated.

Polyclonal, antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet, hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with 1/5 to {fraction 1/10)} the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibody refers to art antibody obtained from a population of substantially homogeneous antibodies. Monoclonal antibodies are generally highly specific, and may be directed against a single antigenic site. In contrast to conventional (polyclonal), antibody preparations that typically include different antibodies directed against different determinants (epitopes). In addition to their specificity, the monoclonal antibodies are advantageous in that they are synthesized by the homogeneous culture, uncontaminated by other immunoglobulins with different specificities and characteristics.

Monoclonal antibodies may be made by the hybridoma method first described by Kohler et al., (*Nature*, 256:495-7, 1975), or may be made by recombinant DNA methods (see, e.g., U.S. Pat. No. 4,816,567). The monoclonal antibodies may also be isolated from display libraries (e.g., yeast libraries, phage antibody libraries) using the techniques described in, for example, Clackson et al., (*Nature* 352:624-628, 1991), Marks et al., (*J. Mol. Biol.* 222:581-597, 1991) Hoogenboom (Nat Biotechnol. 23:1105-16,2005) and Mondon et al., (*Front Biosci.*, 13:1117-1129, 2008).

In the hybridoma method, a mouse or other appropriate host animal, such, as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, *J. Immunol.*, 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

It is further contemplated that antibodies may be used as smaller antigen binding fragments of the antibody well-known in the art and described herein.

The present disclosure encompasses IL-1 (e.g., IL-1β) binding antibodies that include two full length heavy chains and two full length light chains. Alternatively, the IL-1β binding antibodies can be constructs such as single chain antibodies or "mini" antibodies that retain binding activity to IL-1β. Such constructs can be prepared by methods known in the art such as, for example, the PCR mediated cloning and assembly of single chain antibodies for expression in $E.$ $coli$ (as described in Antibody Engineering, The practical approach series, J. McCafferty, H. R. Hoogenboom, and D. J. Chiswell, editors, Oxford University Press, 1996). In this type of construct, the variable portions of the heavy and light chains of an antibody molecule are PCR amplified from cDNA. The resulting amplicons are then assembled, for example, in a second PCR step, through a linker DNA that encodes a flexible protein linker composed of the amino acids Gly and Ser. This linker allows the variable heavy and light chain portions to fold in such a way that the antigen binding pocket is regenerated and antigen is bound with affinities often comparable to the parent full-length dimeric immunoglobulin molecule.

The IL-1 (e.g., IL-1β) binding antibodies and binding fragments of the present disclosure encompass variants of the exemplary antibodies, fragments and sequences disclosed herein. Variants include peptides and polypeptides comprising one or more amino acid sequence substitutions, deletions, and/or additions that have the same or substantially the same affinity and specificity of epitope binding as one or more of the exemplary antibodies, fragments and sequences disclosed herein. Thus, variants include peptides and polypeptides comprising one or more amino acid sequence substitutions, deletions, and/or additions to the exemplary antibodies, fragments and sequences disclosed herein where such substitutions, deletions and/or additions do not cause substantial changes in affinity and specificity of epitope binding. For example, a variant of an antibody or fragment may result from one or more changes to an antibody or fragment, where the changed antibody or fragment has the same or substantially the same affinity and specificity of epitope binding as the starting sequence. Variants may be naturally occurring, such as allelic or splice variants, or may be artificially constructed. Variants may be prepared from the corresponding nucleic acid molecules encoding said variants. Variants of the present antibodies and IL-1β binding fragments may have changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of IL-1 (e.g., IL-1β) binding antibodies and binding fragments may also be prepared by mutagenesis techniques. For example, amino acid changes may be introduced at random throughout an antibody coding region and the resulting variants may be screened for binding affinity for IL-1β or for another property. Alternatively, amino acid changes may be introduced in selected regions of an IL-1β antibody, such as in the light and/or heavy chain CDRs, and/or in the framework regions, and the resulting antibodies may be screened for binding to IL-1β or some other activity. Amino acid changes encompass one or more amino acid substitutions in a CDR, ranging from a single amino acid difference to the introduction of multiple permutations of amino acids within a given CDR, such as CDR3. In another method, the contribution of each residue within a CDR to IL-1β binding may be assessed by substituting at least one residue within the CDR with alanine, Lewis et al. (1995), Mol. Immunol. 32: 1065-72. Residues which are not optimal for binding to IL-1β may then be changed in order to determine a more optimum sequence. Also encompassed are variants generated by insertion of amino acids to increase the size of a CDR, such as CDR3. For example, most light chain CDR3 sequences are nine amino acids in length. Light chain sequences in an antibody which are shorter than nine residues may be optimized for binding to IL-1 β by insertion of appropriate amino acids to increase the length of the CDR.

Variants may also be prepared by "chain shuffling" of light or heavy chains, Marks et al. (1992), Biotechnology 10: 779-83. A single light (or heavy) chain can be combined with a library having a repertoire of heavy (or light) chains and the resulting population is screened for a desired activity, such as binding to IL-1β. This permits screening of a greater sample of different heavy (or light) chains in combination with a single light (or heavy) chain than is possible with libraries comprising repertoires of both heavy and light chains.

The IL-1 (e.g., IL-1β) binding antibodies and binding fragments of the present disclosure encompass derivatives of the exemplary antibodies, fragments and sequences disclosed herein. Derivatives include polypeptides or peptides, or variants, fragments or derivatives thereof, which have been chemically modified. Examples include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The IL-1β binding antibodies and binding fragments can be bispecific. Bispecific antibodies or fragments can be of several configurations, for example, bispecific antibodies may resemble single antibodies (or antibody fragments) but have two different antigen binding sites (variable regions). Bispecific antibodies can be produced by chemical techniques (Kranz et al. (1981), Proc. Natl. Acad. Sci. USA, 78:

5807), by "polydoma" techniques (U.S. Pat. No. 4,474,893) or by recombinant DNA techniques. Bispecific antibodies can have binding specificities for at least two different epitopes, at least one of which is an epitope of IL-1β. The IL-1β binding antibodies and binding fragments can also be heteroantibodies. Heteroantibodies are two or more antibodies, or antibody binding fragments (Fab) linked together, each antibody or fragment having a different specificity.

Techniques for creating recombinant DNA versions of the antigen-binding regions of antibody molecules which bypass the generation of monoclonal antibodies are contemplated for the present IL-1 (e.g., IL-1β) binding antibodies and binding fragments. DNA is cloned into a bacterial expression system. One example of such a technique suitable for the practice of this invention uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind IL-1β. Such IL-1β binding agents (Fab fragments with specificity for an IL-1β polypeptide) are specifically encompassed within the IL-1β binding antibodies and binding fragments of the present disclosure.

The present IL-1 (e.g., IL-1β) binding antibodies and binding fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment is a non-human (e.g., mouse) antibody that has been engineered by modifying (e.g., deleting, inserting, or substituting) amino acids at specific positions so as to reduce or eliminate any detectable immunogenicity of the modified antibody in a human.

Humanized antibodies include chimeric antibodies and CDR-grafted antibodies. Chimeric antibodies are antibodies that Include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci. USA,* 81; 6841-6855 (1984), Boulianne, et al., *Nature,* 312; 643-646 (1984), and PCT Application Publication WO 86/01533. Although, they can be less Immunogenic than a mouse monoclonal antibody, administrations of chimeric antibodies have been associated with human anti-mouse antibody responses (MAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), Proc. Natl. Acad. Sci., 81: 6851; Neuberger et al. (1984), Nature, 312; 604. One example is the replacement of a Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody of the Invention can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature,* 321: 522-525 (1986), Riechmann et al. *Nature,* 332: 323-327 (19S8), and Verhoeyen et al., *Science,* 239; 1534-1536 (1988)). Methods that can he used to produce humanized antibodies also are described in U.S. Pat. Nos. 4,816,567, 5,721,167, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature,* 332: 323-327 (1988), and Verhoeyen et al., *Science,* 239: 1534-1536 (1988).

Human engineered antibodies include for example "veneered" antibodies and antibodies prepared using HUMAN ENGINEERING™ technology (see for example, U.S. Pat. Nos. 5,766,886 and 5,869,619), HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or antigen-binding properties. Thus, a low risk position is one for which a substitution is predicted to be beneficial because it is predicted to reduce immunogenicity without significantly affecting antigen binding properties. A moderate risk position is one for which a substitution is predicted to reduce immunogenicity, but is more likely to affect protein folding and/or antigen binding. High risk positions contain residues most likely to be involved in proper folding or antigen binding. Generally, low risk positions in a non-human antibody are substituted with human residues, high risk positions are rarely substituted, and humanizing substitutions at moderate risk positions are sometimes made, although not indiscriminately, Positions with prolines in the non-human antibody variable region sequence are usually classified as at least moderate risk-positions.

The particular human amino acid residue to be substituted at a given low or moderate risk position of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues In the human antibody sequence according to the alignment. Techniques for making human engineered proteins are described in greater detail in Studnicka et al., *Protein Engi-* neering, 7: 805-814 (1994), U.S. Pat. Nos. 5,766,886, 5,770, 196, 5,821,123, and 5,869,619, and PCT Application Publication WO 93/11794.

"Veneered" antibodies are non-human or humanized (e.g., chimeric or COD-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody arid replacing at least one of them with the corresponding surface residues from a human framework region. Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (II) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering*, Springer, New York, N.Y., 2001.

Exemplary humanized or human engineered antibodies include IgG, IgM, IgE, IgA, and IgD antibodies. The present antibodies can be of any class (IgG, IgA, IgM, IgE, IgD, etc) or isotype and can comprise a kappa or lambda light chain, for example, a human antibody can comprise an IgG heavy chain or defined fragment, such as at least one of isotypes, IgG1, IgG2, IgG3 or IgG4. As a further example, the present antibodies or fragments can comprise an IgG1 heavy chain and an IgG1 light chain.

The present antibodies and fragments can be human antibodies, such as antibodies which bind IL-1β polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,398 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat Biotechnol.* 14:845-851, 1996), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102, 2002) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4), immunization of the TC MOUSE™ with various human antigens produces antibody responses comprising human antibodies.

See also Jakobovits et al., *Proc. Natl. Acad. Sci. USA*, 90:2551 (1993); Jakobovits et al., *Nature*, 362:255-258 (1993); Bruggermann et al., *Year in Immunol.*, 7:33 (1993); and U.S. Pat. Nos. 5,591,669, 5,589,369, 5,545,807; and U.S Patent Publication. No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human antibodies can also be generated through the in vitro screening of antibody display libraries. See Hoogenboom et al. (1991), J. Mol. Biol. 227: 381; and Marks et al. (1991), J. Mol. Biol. 222: 581. Various antibody-containing phage display libraries have been described and may be readily prepared. Libraries may contain a diversity of human antibody sequences, such as human Fab, Fv, and scFv fragments, that may be screened against an appropriate target. Phage display libraries may comprise peptides or proteins other than antibodies which may be screened to identify selective binding agents of IL-1β.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The disclosure contemplates a method for producing target-specific antibody or antigen-binding portion thereof comprising the steps of synthesizing a library of human antibodies on phage, screening the library with target protein or a portion thereof, isolating phage that bind target, and obtaining the antibody from the phage. By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the invention may be obtained in this way.

Phage-display processes mimic immune selection through the display of antibody repertoires on the surface of filamentous bacteriophage, and subsequent selection of phage by their binding to an antigen of choice. One such technique Is described in WO 99/10494, which describes the isolation of high affinity and functional agonistic antibodies for MPL and msk receptors using such an approach. Antibodies of the Invention can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used In generating and screening antibody display libraries (see, e.g., Ladner et al. U.S. Pat. No. 5,223,409; Rang et al. PCT Publication No. WO 92/18619; Dower et al. PCT Publication No. WO 91/17271; Winter et al. PCT Publication No. WO 92/20791; Maryland et al. PCT Publication No, WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) Science 246:1275-1231; McCafferty et al., Nature (1990) 348:552-554; Griffiths et al. (1993) *EMBO J* 12:725-734; Hawkins et al. (1992) *J. Mol. Biol.* 226:889-896; Clackson et al. (1991) Nature 352:024-628; Gram et al. (1992) *Proc. Natl. Acad. Sci. USA* 89:3576-3580; Garrad et al. (1991) *Bio/Technology* 9:1373-1377; Hoogenboom et al. (1991) Nuc Acid Res 19:4133-4137; and Barbas et al (1991) *Proc. Natl. Acad. Sci. USA* 88:7978-7982.

In one embodiment, to isolate human antibodies specific for the target antigen with the desired characteristics, a Human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 02/01047, McCafferty et al., (*Nature* 348:552-554, 1990); and Griffiths et al., (*EMBO J* 12:725-734, 1993). The scFv antibody libraries preferably are screened using target protein as the antigen.

Alternatively, the Fd fragment ($V_H$-$C_H$1) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol.* 222:581-597 (1991); U.S. Pat. Nos. 5,565,332 and 5,573,905; Clackson, T. and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Annu. Rev. Immunol.* 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178: 187-193 (2062), and U.S. patent publication no, 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, Ifl, Ike, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for target binding, are performed to select preferred $V_L$/$V_H$ pair combinations. Additionally, to further improve the quality of the antibody, the $V_L$ and $V_H$ segments of the preferred $V_L$/$V_H$ pair(s) can be randomly mutated, preferably within the any of the CDR1, CDR2 or CDR3 region of $V_H$ and/or $V_L$ in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such, that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be earned out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage-display techniques such as those described therein. This technique is also disclosed in Marks et al, (*Bio/Technology*, 10:779-783, 1992).

Methods for display of peptides on the surface of yeast and microbial cells have also been used to identify antigen specific antibodies. See, for example, U.S. Pat. No. 6,699,658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial ceil display methods. Selection of polypeptide using ribosome display is described in Hanes et al., (*Proc. Natl Acad Sci USA*, 94:4937-4942, 1997) and U.S. Pat. Nos. 5,643, 768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

The IL-1 (e.g., IL-1β) binding antibodies and binding fragments may comprise one or more portions that do not bind IL-1β but instead are responsible for other functions, such as circulating half-life, direct cytotoxic effect, detectable labeling, or activation of the recipient's endogenous complement cascade or endogenous cellular cytotoxicity. The antibodies or fragments may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the invention may include an epitope tag, a salvage receptor epitope, a label moiety for diagnostic or purification purposes, or a cytotoxic moiety such as a radionuclide or toxin.

The constant region (when present) of the present antibodies and fragments may be of the γ1, γ2, γ3, γ4, μ, β2, or δ or ε type, preferably of the γ type, more preferably of the γ, type, whereas the constant part of a human light chain may be of the κ or λ type (which includes the $\lambda_1$, $\lambda_2$ and $\lambda_3$ subtypes) but is preferably of the κ type.

Variants also include antibodies or fragments comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity.

For example, the present IL-1β binding antibodies and binding fragments may comprise a modified Fc region, Fc region refers to naturally-occurring or synthetic polypeptides homologous to the IgG C-terminal domain that is produced upon papain digestion of IgG. IgG Fc has a molecular weight of approximately 50 kD. In the present antibodies and fragments, an entire Fc region can be used, or only a half-life enhancing portion. In addition, many modifications in amino acid sequence are acceptable, as native activity is not in all cases necessary or desired.

The Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor with high affinity. Various mutations for human IgG also are known (see, e.g., Morrison et al., 1994, The Immunologist 2: 119 124 and Brekke et al., 1994, The Immunologist 2: 125).

In some embodiments, the present antibodies or fragments are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described In U.S. Pat. No. 6,998, 253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope Into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., $IgG_1$, $IgG_2$, $IgG_3$, or $IgG_4$) that is responsible for increasing the in vivo serum half-life of the IgG molecule.

A salvage receptor binding epitope can include a region wherein any one or more amino acid residues from one or two loops of a Fc domain are transferred to an analogous position of the antibody fragment Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Mutation of residues within Fc receptor binding sites can result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position). For example it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., *Mol Immunol.* 30:105-8, 1993).

Antibody fragments are portions of an intact full length antibody, such as an antigen binding or variable region of the intact antibody. Examples of antibody fragments include Fab, Fab', $F(ab')_2$, and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), adnectins, binding-domain immunoglobulin fusion proteins; camelized antibodies; $V_{HH}$ containing antibodies; and any other polypeptides formed from antibody fragments.

The present disclosure includes IL-1β binding antibody fragments comprising any of the foregoing heavy or light chain sequences and which bind IL-1β. The term fragments as used herein refers to any 3 or more contiguous amino acids (e.g., 4 or more, 5 or more 6 or more, 8 or more, or even 10 or more contiguous amino acids) of the antibody and encompasses Fab, Fab', $F(ab')_2$, and F(v) fragments, or the individual light, or heavy chain variable regions or portion thereof IL-1β binding fragments include, for example, Fab, Fab', $F(ab')_2$, Fv and scFv. These fragments lack the Fc fragment of an intact antibody, clear more rapidly from the circulation, and can have less non-specific tissue binding than an intact antibody. See Wahl et al. (1983), J. Nucl. Med., 24: 316-25. These fragments can he produced from intact antibodies using well known methods, for example by proteolytic cleavage with enzymes such as papain (to produce Fab fragments) or pepsin (to produce $F(ab')_2$ fragments).

In vitro and cell based assays are well described in the art for use in determining binding of IL-1β to IL-1 receptor type I (IL-1R1), including assays that determining in the presence of molecules (such as antibodies, antagonists, or other inhibitors) that bind to IL-1β or IL-1R1. (see for example Evans et al., (1995), J. Biol. Chem. 270:11477-11483; Vigers et al., (2000), J. Biol. Chem. 275:36927-36933; Yanofsky et al., (1996), Proc. Natl. Acad. Sci. USA 93:7381-7386: Fredericks et al., (2004), Protein Eng. Des. Sel. 17:95-106; Slack et al., (1993), J. Biol. Chem. 268:2513-2524; Smith et al., (2003), Immunity 18:87-96; Vigers et al., (1997), Nature 386:190-194, Ruggiero et al., (1997), J. Immunol. 158:3881-3887; Guo et al., (1995), J. Biol. Chem. 270:27562-27568; Svenson et al., (1995), Eur. J. Immunol. 25:2842-2850; Arend et al., (1994), J. Immunol. 153:4766-4774). Recombinant IL-1 receptor type I, including human IL-1 receptor type I, for such assays is readily available from a variety of commercial sources (see for example R&D Systems, SIGMA). IL-1 receptor type I also can be expressed from an expression construct or vector introduced into an appropriate host cell using standard molecular biology and transfection techniques known in the art. The expressed IL-1 receptor type I may then be isolated and purified for use in binding assays, or alternatively used directly in a cell associated form.

For example, the binding of IL-1β to IL-1 receptor type I may be determined by immobilizing an IL-1β binding antibody, contacting IL-1β with the immobilized antibody and determining whether the IL-1β was bound to the antibody, and contacting a soluble form of IL-1R1 with the bound IL-1β/antibody complex and determining whether the soluble IL-1R1 was bound to the complex. The protocol may also include contacting the soluble IL-1R1 with the immobilized antibody before the contact with IL-1β, to confirm that the soluble IL-1R1 does not bind to the immobilized antibody. This protocol can be performed using a Biacore® Instrument for kinetic analysis of binding interactions. Such a protocol can also be employed to determine whether an antibody or other molecule permits or blocks the binding of IL-1β to IL-1 receptor type I.

For other IL-1β/IL-1R1 binding assays, the permitting or blocking of IL-1β binding to IL-1 receptor type I may be determined by comparing the binding of IL-1β to IL-1R1 in the presence or absence of IL-1β antibodies or IL-1β binding fragments thereof. Blocking is identified in the assay readout as a designated reduction of IL-1β binding to IL-1 receptor type I in the presence of anti-IL-1β antibodies or IL-1β binding fragments thereof as compared to a control sample that contains the corresponding buffer or diluent but not an IL-1β antibody or IL-1β binding fragment thereof. The assay readout may be qualitatively viewed as indicating the presence or absence of blocking, or may be quantitatively viewed as indicating a percent or fold reduction in binding due to the presence of the antibody or fragment.

Alternatively or additionally, when an IL-1β binding antibody or IL-1β binding fragment substantially blocks IL-1β binding to IL-1R1, the IL-1β binding to IL-1R1 is reduced by at least 10-fold, alternatively at least about 20-fold, alternatively at least about 50-fold, alternatively at least about 100-fold, alternatively at least about 1000-fold, alternatively at least about 10000-fold, or more, compared to binding of the same concentrations of IL-1β and IL-1R1 in the absence of the antibody or fragment. As another example, when an IL-1β binding antibody or IL-1β binding fragment substantially permits IL-1β binding to IL-1R1, the IL-1β binding to IL-1R1 is at least about 90%, alternatively at least about 95%, alternatively at least about 99%, alternatively at least about 99.9%, alternatively at least about 99.99%, alternatively at least about 99.999%, alternatively at least about 99.9999%, alternatively substantially identical to binding of the same concentrations of IL-1β and IL-1R1 in the absence of the antibody or fragment.

The present disclosure may in certain embodiments encompass IL-1β binding antibodies or IL-1β binding fragments that bind to the same epitope or substantially the same epitope as one or more of the exemplary antibodies described herein. Alternatively or additionally, the IL-1β binding antibodies or IL-1β binding fragments compete with the binding of an antibody having variable region sequences of AB7, described in U.S. application Ser. No. 11/472,813 or WO 2007/002261 (sequences shown below). As an example, when an IL-1β binding antibody or IL-1β binding fragment competes with the binding of an antibody having the light chain variable region of SEQ ID NO:5 and the heavy chain variable region, of SEQ ID NO:6, binding of an antibody having the light chain variable region, of SEQ ID NO:5 and the heavy chain variable region of SEQ ID NO:6 to IL-1β may be reduced by at least about 2-fold, alternatively at least about 5-fold, alternatively at least about 10-fold, alternatively at least about 20-fold, alternatively at least about 50-fold, alternatively at least about 100-fold, alternatively at least about 1000-fold, alternatively at least about 10000-fold, or more, if the binding is measured in the presence of the IL-1β binding antibody or IL-1β binding fragment. The IL-1β binding antibody or IL-1β binding fragment may be present in excess of the antibody having the light chain variable region of SEQ ID NO:5 and the heavy chain variable region of SEQ ID NO:6, for example an excess of least about 2-fold, alternatively at least about 5-fold, alternatively at least about 10-fold alternatively at least about 20-fold, alternatively at least about 50-fold, alternatively at least about 100-fold, alternatively at least about 1000-fold, alternatively at least about 10000-fold. Alternatively or additionally, the present disclosure encompasses IL-1β binding antibodies and fragments that bind to an epitope contained in the amino acid sequence ESVDPKNYPKKKMEKRFVFNKIE (SEQ ID NO: 1) (U.S. application Ser. No. 11/472,813, WO 2007/002251) which corresponds to residues 83-105 of the mature IL-1β protein. As contemplated herein, one can readily determine if an IL-1β binding antibody or fragment binds to the same epitope or substantially the same epitope as one or more of the exemplary antibodies, such as for example the antibody designated AB7, using any of several known methods in the art.

For example, the key amino acid residues (epitope) bound by an IL-1β binding antibody or fragment may be determined using a peptide array, such as for example, a PepSpot™ peptide array (JPT Peptide Technologies, Berlin, Germany), wherein a scan of twelve amino-acid peptides, spanning the entire IL-1β amino acid sequence, each peptide overlapping by 11 amino acid to the previous one, is synthesized directly on a membrane. The membrane carrying the peptides is then probed with the antibody for which epitope binding information is sought, for example at a concentration of 2 μg/ml, for 2 hr at room temperature. Binding of antibody to membrane bound peptides may be detected using a secondary HRP-conjugated goat anti-human (or mouse, when appropriate) antibody, followed by enhanced chemiluminescence (ECL). The peptides spot(s) corresponding to particular amino acid residues or sequences of the mature IL-1β protein, and which score positive for antibody binding, are indicative of the epitope bound by the particular antibody.

Alternatively or in addition, antibody competition experiments may be performed and such assays are well known in the art. For example, an antibody of unknown specificity may be compared with any of the exemplary of antibodies (e.g., AB7) of the present disclosure. Binding competition assays may be performed, for example, using a Biacore® instrument for kinetic analysis of binding interactions or by ELISA. In such an assay, the antibody of unknown epitope specificity is evaluated for its ability to compete for binding against the known comparator antibody (e.g., AB7). Competition for binding to a particular epitope is determined by a reduction in binding to the IL-1β epitope of at least about 50%, or at least about 70%, or at least about 80%, or at least about 90%, or at least about 95%, or at least about 99% or about 100% for the known comparator antibody (e.g., AB7) and is indicative of binding to substantially the same epitope.

In view of the identification in this disclosure of IL-1β binding regions in exemplary antibodies and/or epitopes recognized by the disclosed antibodies, it is contemplated that additional antibodies with similar binding characteristics and therapeutic or diagnostic utility can be generated that parallel the embodiments of this disclosure.

Antigen-binding fragments of an antibody include fragments that retain the ability to specifically bind to an antigen, generally by retaining the antigen-binding portion of the antibody. It is well established that the antigen-binding function of an antibody can be performed by fragments of a full-length antibody. Examples of antigen-binding portions include (i) a Fab fragment, which is a monovalent fragment consisting of the VL, VH, CL and CH1 domains; (ii) a F(ab')$_2$ fragment, which is a bivalent fragment comprising two Fab fragments linked by a disulfide bridge at the hinge region; (iii) a Fd fragment which is the VH and CH1 domains; (iv) a Fv fragment which is the VL and VH domains of a single arm of an antibody, (v) a dAb fragment (Ward et al., (1989) Nature 341:544-540), which is a VH domain; and (vi) an isolated complementarity determining region (CDR). Single chain antibodies are also encompassed within the term antigen-binding portion of an antibody. The IL-1β binding antibodies and fragments of the present invention also encompass monovalent or multivalent, or monomeric or multimeric (e.g. tetrameric), CDR-derived binding domains with or without a scaffold (for example, protein or carbohydrate scaffolding).

The present IL-1β binding antibodies or binding fragments may be part of larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibodies and fragments comprising immunoadhesion molecules can be obtained using standard recombinant DNA techniques, as described herein. Preferred antigen binding portions are complete domains or pairs of complete domains.

The IL-1β binding antibodies and binding fragments may also encompass domain antibody (dAb) fragments (Ward et al., Nature 341:544-546, 1989) which consist of a $V_H$ domain. The IL-1β binding antibodies and fragments of the present invention also encompass diabodies, which are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

The IL-1β binding antibodies and binding fragments of the present disclosure also encompass single-chain antibody fragments (scFv) that bind to IL-1β. An scFv comprises an antibody heavy chain variable region ($V_H$) operably linked to an antibody light chain variable region ($V_L$) wherein the heavy chain variable region and the light chain variable region, together or individually, form a binding site that binds IL-1β. An scFv may comprise a $V_H$ region at the ammo-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883).

An scFv may optionally further comprise a polypeptide linker between the heavy chain variable region and the light chain variable region. Such polypeptide linkers generally comprise between 1 and 50 amino acids, alternatively between 3 and 12 amino acids, alternatively 2 amino acids. An example of a linker peptide for linking heavy and light chains in an scFv comprises the 5 amino acid sequence Gly-Gly-Gly-Gly-Ser (SEQ ID NO: 2). Other examples comprise one or more tandem repeats of this sequence (for example, a polypeptide comprising two to four repeats of Gly-Gly-Gly-Gly-Ser (SEQ ID NO: 2) to create linkers.

The IL-1β binding antibodies and binding fragments of the present invention also encompass heavy chain antibodies (HCAb), Exceptions to the $H_2L_2$ structure of conventional antibodies occur in some isotypes of the immunoglobulins found in camelids (camels, dromedaries and llamas; Hamers-Casterman et al., 1993 Nature 363: 446; Nguyen et al., 1998 J. Mol. Biol. 275; 413), wobbegong sharks (Nuttall et al., *Mol. Immunol.* 38:313-26, 2001), nurse sharks (Greenberg et al., Nature 374:168-73, 1995; Roux et al., 1998 Proc. Nat. Acad. Sci. USA 95: 11804), and in the spotted ratfish (Nguyen, et al., "Heavy-chain antibodies in *Camelidae*; a case of evolutionary innovation," 2002 Immunogenics 54(1): 39-47). These antibodies can apparently form antigen-binding regions using only heavy chain variable regions, in that these functional antibodies are dimers of heavy chains only (referred to as "heavy-chain antibodies" or "HCAbs"). Accordingly, some embodiments of the present IL-1β binding antibodies and fragments may be heavy chain antibodies that specifically bind to IL-1β. For example, heavy chain antibodies that, are a class of IgG and devoid of light chains are produced by animals of the genus *Camelidae* which includes camels, dromedaries and llamas (Hamers-Casterman et al., Nature 363:446-448 (1993)). HCAbs have a molecular weight of about 95 kDa instead of the about 160 kDa molecular weight of conventional IgG antibodies. Their binding domains consist only of the heavy-chain variable domains, often referred to as $V_{HH}$ to distinguish them from conventional $V_H$. Muyldermans et al., J. Mol. Recognit. 12:131-140 (1999). The variable domain of the heavy-chain antibodies is sometimes referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods.

Since the first constant domain ($C_{H1}$) is absent (spliced out during mRNA processing due to loss of a splice consensus signal), the variable domain ($V_{HH}$) is immediately followed by the hinge region, the $C_{H2}$ and the $C_{H3}$ domains (Nguyen et al., Mol. Immunol. 36:515-524 (1999): Woolven et al., Immunogenetics 50:98-101 (1999)). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains.

Although the HCAbs are devoid of light chains, they have an antigen-binding repertoire. The genetic generation mechanism of HCAbs is reviewed in Nguyen et al. Adv. Immunol 79:261-296 (2001) and Nguyen et al. Immunogenetics 54:39-47 (2002). Sharks, including the nurse shark, display similar antigen receptor-containing single monomeric V-domains. Irving el al., J. Immunol. Methods 248:31-45 (2001); Roux el al., Proc. Natl. Acad. Sci. USA 95:11804 (1998).

$V_{HH}$s comprise small intact antigen-binding fragments (for example, fragments that are about 15 kDa, 118-136 residues). Camelid $V_{HH}$ domains have been found to bind to antigen with high affinity (Desmyter et al., *J. Biol. Chem.* 276:26283-90, 2001), with $V_{HH}$ affinities typically in the nanomolar range and comparable with those of Fab and scFv fragments. $V_{HH}$s are highly soluble and snore stable than the corresponding derivatives of scFv and Fab fragments. $V_H$ fragments have been relatively difficult to produce in soluble form, but improvements in solubility and specific binding can be obtained when framework residues are altered to be more $V_{HH}$-like. (See, for example, Reichman et al., J Immunol Methods 1999, 231:25-38.) $V_{HH}$s carry amino acid substitutions that make them more hydrophilic and prevent prolonged interaction with BiP (immunoglobulin heavy-chain binding protein), which normally hinds to the H-chain in the Endoplasmic Reticulum (BR) during folding and assembly, until it is displaced by the L-chain. Because of the $V_{HH}$s' increased hydrophilicity, secretion from the ER is improved.

Functional $V_{HH}$s may be obtained by proteolytic cleavage of HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$S in phage display is much simpler and more efficient compared to Fabs or scFvs, since only one domain needs to be cloned and expressed to obtain a functional antigen-binding fragment. Muyldermans, Biotechnol., 74:277-302 (2001): Ghahroudi et al., FEBS Lett. 414:521-520 (1997); and van der Linden et al., J. Biotechnol. 80:261-270 (2000). Methods for generating antibodies having camelid heavy chains are also described in U.S. Patent Publication Nos. 20050136049 and 20050037412.

Ribosome display methods may be used to identify and isolate scFv and/or $V_L$s molecules having the desired binding activity and affinity. Irving et al., J. Immunol. Methods 248: 31-45 (2001). Ribosome display and selection has the potential to generate and display large libraries ($10^{14}$).

Other embodiments provide $V_{HH}$-like molecules generated through the process of camelsation, by modifying non-*Camelidae* $V_H$s, such as human $V_{HH}$s, to improve their solubility and prevent non-specific binding. This is achieved by replacing residues on the $V_L$s side of $V_H$s with $V_{HH}$-like residues, thereby mimicking the more soluble $V_{HH}$ fragments. Camelised $V_H$ fragments, particularly those based on the human framework, are expected to exhibit a greatly reduced immune response when administered in vivo to a patient and, accordingly, are expected to have significant advantages for therapeutic applications. Davies et al., FEBS Lett. 339:285-290 (1994); Davies et al., Protein Eng. 9:531-537 (1996); Tanha et al., J. Biol. Chem. 276:24774-24780 (2001); and Riechmann et al., Immunol. Methods 231:25-38 (1999).

A wide variety of expression systems are available for the production of IL-1β binding fragments including Fab fragments, scFv, and V$_{HH}$s. for example, expression systems of both prokaryotic and eukaryotic origin may be used for the large-scale production of antibody fragments and antibody fusion proteins. Particularly advantageous are expression systems that permit the secretion of large amounts of antibody fragments into the culture medium.

Production of bispecific Fab-scFv ("bibody") and trispecific Fab-(scFv) (2) ("tribody") are described in Schoonjans et al. (*J Immunol.* 165:7050-57, 2000) and Willems et al. (*J Chromatogr B Analyt Technol Biomed Life Sci.* 786:161-76, 2003). For dibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab. A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

The IL-1β binding antibodies and binding fragments also encompass antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

IL-1β binding antibodies and binding fragments of the present disclosure also encompass immunoadhesins. One or more CDRs may be incorporated into a molecule either covalently or noncovalently to make it an immunoadhesin. An immunoadhesin may incorporate the CDR(s) as part of a larger polypeptide chairs, may covalently link the CDR(s) to another polypeptide chain, or may incorporate the CDR(s) noncovalently. The CDRs disclosed herein permit the immunoadhesin to specifically bind to IL-1β.

The IL-1β binding antibodies and fragments also encompass antibody mimics comprising one or more IL-1β binding portions built on an organic or molecular scaffold (such as a protein or carbohydrate scaffold). Proteins having relatively defined three-dimensional structures, commonly referred to as protein scaffolds, may be used as reagents for the design of antibody mimics. These scaffolds typically contain one or more regions which are amenable to specific or random sequence variation, and such sequence randomization is often carried out to produce libraries of proteins from which desired products may be selected. For example, an antibody mimic can comprise a chimeric non-immunoglobulin binding polypeptide having an immunoglobulin-like domain containing scaffold having two or more solvent exposed loops containing a different CDR from a parent antibody inserted into each of the loops and exhibiting selective binding activity toward a ligand bound by the parent antibody. Non-immunoglobulin protein scaffolds have been proposed for obtaining proteins with novel binding properties. (Tramontano et al. J. Mol. Recognit. 7:9, 1994; McConnell and Hoess, J. Mol. Biol. 250:460, 1995). Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995). Methods for employing scaffolds for antibody mimics are disclosed in U.S. Pat. No. 5,770,380 and US Patent Publications 2004/0171116, 2004/0266993, and 2005/0038229.

Preferred IL-1β antibodies or antibody fragments for use in accordance with the Invention generally bind to human IL-1β with high affinity (e.g., as determined with BIACORE, as determined by KinExA), such as for example with an equilibrium binding dissociation constant ($K_D$) for IL-1β of about 10 nM or less, about 5 nM or less, about 2 nM or less, or preferably about 1 nM or less, about 500 pM or less, or more preferably about 250 pM or less, about 100 pM or less, about 50 pM or less, about 25 pM or less, about 10 pM or less, about 5 pM or less, about 3 pM or less about 1 pM or less, about 0.75 pM or less, about 0.5 pM or less, or about 0.3 pM or less. The dissociation constant may be measured, for example, using Biacore (GE Healthcare), and measurement using Biacore may be preferred when the dissociation constant is greater than about 10 pM. Alternatively or in addition, the dissociation constant may be measured using KinExA (Sapidyne Instruments, Inc), and measurement using KinExA may be preferred when the dissociation constant is less than about 10 pM.

Antibodies or fragments of the present invention may, for example, bind to IL-1β with an $IC_{50}$ of about 10 nM or less, about 5 nM or less, about 2 nM or less, about 1 nM or less, about 0.75 nM or less, about 0.5 nM or less, about 0.4 nM or less, about 0.3 nM or less, or even about 0.2 nM or less, as determined by enzyme linked immunosorbent assay (ELISA). Preferably, the antibody or antibody fragment of the present invention docs not cross-react with any target other than IL-1. for example, the present antibodies and fragments may bind to IL-1β, but do not detectably bind to IL-1α, or have at least about 100 times (e.g., at least about 150 times, at least about 200 times, or even at least about 250 times) greater selectivity in its binding of IL-1β relative to its binding of IL-1α. Antibodies or fragments used according to the invention may, in certain embodiments, inhibit IL-1β induced expression of serum-IL-6 in an animal by at least 50% (e.g., at least 60%, at least 70%, or even at least 80%) as compared to the level of serum IL-6 in an IL-1β stimulated animal that has not been administered an antibody or fragment of the invention. Antibodies may bind IL-1β but permit or substantially permit the binding of the bound IL-1β ligand to IL-1 receptor type 1 (IL-1R1). In contrast to many known IL-1β binding, antibodies, that block or substantially interfere with binding of IL-1β to IL-1R1, the antibodies designated AB5 and AB7 (U.S. Pat. No. 7,531,166) selectively bind to the IL-1β ligand, but permit the binding of the bound IL-1β ligand to IL-1R1. For example, the antibody designated AB7 binds to an IL-1β epitope but still permits the bound IL-1β to bind to IL-1R1. In certain embodiments, the antibody may decrease the affinity of interaction of bound IL-1β to bind to IL-1R1. Accordingly, the disclosure provides, in a related aspect, use of an IL-1β binding antibody or IL-1β binding antibody fragment that has at least one of the aforementioned characteristics. Any of the foregoing antibodies, antibody fragments, or polypeptides of the invention can be humanized or human engineered, as described herein.

A variety of IL-1 (e.g., IL-1β) antibodies and fragments known in the art may be used as provided by the disclosure herein, including for example antibodies and antibody binding fragments (e.g., V-region sequences) described in, or derived using methods described in the following patents and patent applications: U.S. Pat. No. 4,935,343; US 2003/0026806; US 2003/0124617 (e.g., antibody AAL160); U.S. Pat. No. 7,566,772 (e.g., antibody 9.5.2); WO 03/034984; WO 95/01997 (e.g., antibody SK48-E26 VTKY); U.S. Pat. No. 7,446,175 (e.g., antibody ACZ 885); WO 03/010282 (e.g., antibody Hu007); WO 03/073982 (e.g., antibody N55S), U.S. Pat. No. 7,541,033 (e.g., W17, U43, W13, W18, W20), U.S. Pat. No. 7,491,392, WO 2004/072116, WO 2004/067568, EP 0 267 611 B1, EP 0 364 778 B1, and U.S. application Ser. No. 11/472,813. As a non-limiting example, antibodies AB5 and AB7 (U.S. Pat. No. 7,531,166) may be used in accordance with the invention. Variable region sequences of AB5 and AB7 (also referred to as XOMA 052) are as follows:

```
AB5
LIGHT CHAIN
                                           (SEQ ID NO: 3)
DIQMTQTTSSLSASLGDRVTISCRASQDISNYLSWYQQKPDGTVKLLIY

YTSKLHSGVPSRFSGSGSGTDYSLTISNLEQEDIATYFCLQGKMLPWTF

GGGTKLEIK
```

The underlined sequences depict (from left to right) CDR1, 2 and 3.

```
HEAVY CHAIN
                                           (SEQ ID NO: 4)
QVTLKESGPGILKPSQTLSLTCSFSGFSLSTSGMGVGWIRQPSGKGLEW

LAHIWWDGDESYNPSLKTQLTISKDTSRNQVFLKITSVDTVDTATYFCA

RNRYDPPWFVDWGQGTLVTVSS
```

The underlined sequences depict (from left to right) CDR 1, 2 and 3.

```
AB7
LIGHT CHAIN
                                           (SEQ ID NO: 5)
DIQMTQSTSSLSASVGDRVTITCRASQDISNYLSWYQQKPGKAVKLLIY

YTSKLHSGVPSRFSGSGSGTDYTLTISSLQQEDFATYFCLQGKMLPWTF

GQGTKLEIK
```

The underlined sequences depict (from left to right) CDR1, 2 and 3.

```
HEAVY CHAIN
                                           (SEQ ID NO: 6)
QVQLQESGPGLVKPSQTLSLTCSFSGFSLSTSGMGVGWIRQPSGKGLEW

LAHIWWDGDESYNPSLKSRLTISKDTSKNQVSLKITSVTAADTAVYFCA

RNRYDPPWFVDWGQGTLVTVSS
```

The underlined sequences depict (from left to right) CDR1, 2 and 3.

The antibodies and antibody fragments described herein can be prepared by arty suitable method. Suitable methods for preparing such antibodies and antibody fragments are known in the art. Other methods for preparing the antibodies and antibody fragments are as described herein as part of the invention. The antibody, antibody fragment, or polypeptide of the invention, as described herein, can be isolated or purified to any degree. As used herein, an isolated compound is a compound that has been removed from its natural environment. A purified compound is a compound that has been increased in purity, such that the compound exists in a form that Is more pure than it exists (i) in its natural environment or (ii) when initially synthesized and/or amplified under laboratory conditions, wherein "purity" is a relative term and does not necessarily mean "absolute purity."

Compositions

IL-1 (e.g., IL-1β) binding antibodies and binding fragments can he formulated in compositions, especially pharmaceutical compositions, for use in the methods disclosed herein. Such compositions comprise a therapeutically or prophylactically effective amount of art IL-1β binding antibody or antibody fragment in admixture with a suitable carrier, e.g., a pharmaceutically acceptable agent. Typically, IL-1β binding antibodies and binding fragments are sufficiently purified for administration to an animal (e.g., human) before formulation in a pharmaceutical composition.

Pharmaceutically acceptable agents include for example, carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorohexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in *Remington's Pharmaceutical Sciences*, 18th Edition, A.R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 1.0 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly (ethylene glycol) phenyl ethers (e.g. Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-laurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intrarectal, transdermal, oral, and inhaled routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils, intravenous vehicles include fluid and nutrient replenishes, electrolyte replenishers, such as those based on Ringer's dextrose, and the like. Preservatives and other additives may also be present, such as, for example, antimicrobials, antioxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) sustained release and/or increased stability or half-life in a particular local environment. The invention contemplates that in certain embodiments such compositions may include a significantly larger amount of antibody or fragment in the initial deposit, while the effective amount of antibody or fragment actually released and available at any point in time for is in accordance with the disclosure herein an amount much lower than the initial deposit. The compositions can include the formulation of IL-1β binding antibodies, antibody fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly (2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon- (rhIFN-), interleukin-2, and MN rgp120, Johnson et al., Nat. Med., 2:795-799 (1996); Yasuda, Biomed. Ther., 27; 1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 90/07399; and U.S. Pat. No. 5,654,010. The sustained-release formulations of these proteins were developed using poly-lactic-coglycolic-acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al. Biopolymers 22, 547 [1983], R. Langer et al. Chem. Tech. 12, 98 [1982], Sinha et al., J. Control. Release 90, 261 [2003], Zhu et al., Nat. Biotechnol. 18,24 [2000], and Dai et al. Colloids Surf B Biointerfaces 41, 117 [2005].

Bioadhesive polymers are also contemplated for use in or with compositions of the present invention. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Esterified derivatives of hyaluronic acid have been used to produce microspheres for use in delivery that are biocompatible and biodegradable (see for example, Cortivo et al., Biomaterials (1991) 12:727-730; European Publication No. 517,565; International Publication No. WO 96/29998; Illum et al., J. Controlled Rel. (1994) 29:133-141). Exemplary hyaluronic acid containing compositions of the present invention comprise a hyaluronic acid ester polymer in an amount of approximately 0.1% to about 40% (w/w) of an IL-1β binding antibody or fragment to hyaluronic acid polymer.

Both biodegradable and non-biodegradable polymeric matrices can be used to deliver compositions in accordance with the invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, polyethylene glycol), polyethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example WO 04/009664, WO 05/087201, Sawhney, et al., Macromolecules, 1993, 26, 581-587,) that can absorb up to about 90% of its weight in water and further, optionally is cross-linked with multivalent ions or other polymers.

Delivery systems also include non-polymer systems that are lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such, as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485, 045 and 4,544,545; and EP 102,324).

A pharmaceutical composition comprising an IL-1β binding antibody or binding fragment can be formulated for inhalation, such as for example, as a dry powder. Inhalation solutions also can be formulated in a liquefied propellant for aerosol delivery, In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 µm to 5 µm; however, larger particles may be used, for example, if each particle is fairly porous.

Certain formulations containing IL-1β binding antibodies or antibody fragments can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an IL-1β binding antibody or binding fragment in a mixture with nontoxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate: or binding agents, such as starch, gelatin, or acacia; or lubricating agents such as magnesium stearate, stearic acid, or talc.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment Involving each of the formulations described herein are routinely made in the art and is within the ambit of tasks routinely performed in the art. Appropriate dosages can be ascertained through use of appropriate dose-response data.

Additional formulations will be evident in light of the present disclosure, including formulations involving IL-1β binding antibodies and antibody fragments in combination with one or more other therapeutic agents. For example, in some formulations, an IL-1β binding antibody, antibody fragment (e.g., binding fragment), nucleic acid, or vector of the invention is formulated with a second inhibitor of an IL-1 signaling pathway. Representative second inhibitors include, but are not limited to, antibodies, antibody fragments, peptides, polypeptides, compounds, nucleic acids, vectors and pharmaceutical compositions, such as, for example, those described in U.S. Pat. No. 6,899,878, US 2003022869, US 20060094663, US 20050186615, US 20030166069, WO/04022718, WO/05084696, WO/05019259. For example, a composition may comprise an IL-1β binding antibody, antibody fragment, nucleic acid, or vector of the invention in combination with another IL-1β binding antibody, fragment, or a nucleic acid or vector encoding such an antibody or fragment.

The pharmaceutical compositions can comprise IL-1β binding antibodies or binding fragments thereof in combination with other active agents (e.g., other than IL-1β binding antibodies or binding fragments). Alternatively, the pharmaceutical compositions can comprise IL-1β binding antibodies or binding fragments thereof in combination with other pharmaceutical compositions, including, for example, pharmaceutical compositions comprising one or more active agents other than IL-1β binding antibodies or binding fragments). Such combinations are those useful for their intended purpose. The combinations which are part of this invention can be IL-1β antibodies and fragments, such as for example those described herein, and at least one additional agent. Examples of active agents that may be used in combination set forth below are illustrative for purposes and not intended to be limited. The combination can also include more than one additional agent, e.g., two or three additional agents if the combination is such that the formed composition can perform its Intended function.

The disclosure further contemplates that additional pharmaceutical compositions comprising one or more other active agents may be administered separately from the IL-1β binding antibodies or fragments (e.g. concurrent treatment regimen, subject receiving concurrent treatment), and such separate administrations may be performed at the same time or at different times, such as for example the same or different days, or different times of the same day. Administration of the other pharmaceutical compositions and/or active agents may be according to standard medical practices known in the art, or the administration may be modified (e.g., longer intervals between doses, smaller dosage levels, delayed initiation) when used in conjunction with administration of IL-1β binding antibodies or binding fragments, such as disclosed herein.

Pharmaceutical compositions contemplated in the present disclosure include, for example, pharmaceutical compositions comprising one or more active agents, including for example, a non-steroid immunosuppressant, a non-steroid anti-inflammatory and/or a steroid. In some embodiments, the non-steroid immunosuppressant is selected from a nucleic acid (e.g., DNA) synthesis inhibitor, a cyclosporine, a mycophenolate and a colchicine. In some embodiments, the nucleic acid (e.g., DNA) synthesis inhibitor is azathioprine, an alkylating agent, an anti-metabolite (e.g., methotrexate), X-ray therapy, chlorambucil or cyclophosphamide. In some embodiments, the steroid is a steroid hormone selected from prednisone (e.g., methylprenisolone, prednisolone), cortisol, andrenocorticotrophic hormone and a glucocorticoid. In some embodiments, the non-steroid anti-inflammatory is a TNF inhibitor, an IL-6 inhibitor or an IL-17 inhibitor.

Other active agents may include, for example, indomethacin, non-steroidal anti-inflammatory drugs (NSAIDs) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenelozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors, aquaretics, oral glucocorticoids, intra-articular glucocorticoids, colchicine, xanthine-oxidase inhibitors, allopurinol, uricosuric agents, sulfinpyrazone, febuxostat, probenecid, fenofibrate, benemid, angiotensin II receptor antagonists, losartan, thiazides, PEG-uricase, sodium bicarbonate, ethylenediaminetetraacetic acid. Other active agents for combination include steroids such as prednisolone, prednisone, melhylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies and fragments.

Pharmaceutical compositions (e.g., comprising an active agent) may include, for example antimetabolites, such as for example, methotrexate, azathioprine, mycophenolate mofetil, pyrimidine analogues, purine analogues, folate antagonists; T-cell inhibitors/calcineurin inhibitors, such as for example, cycloserine, mycophenolate, FK506/Tacrolimus; alkylating/cytotoxic agents, such as for example, cyclophosphamide, chlorambucil; Intravenous Immunoglobulin; biologic agents, such as for example, Infliximab, Adalimumab, Etanercept; Interleukin-2 receptor antagonists, such as for example, Daclizumab; and Interferon-alpha.

It is further contemplated that an anti-IL-1β antibody or binding fragment administered to a subject in accordance with the disclosure may be administered in combination (e.g., concurrently) with treatment with at least one additional pharmaceutical composition (e.g., comprising an active agent), such as for example any of the aforementioned active agents. In one embodiment, treatment with the at least one active agent is maintained. In another embodiment, treatment with the at least one active agent is reduced (e.g., tapered) or discontinued (e.g., when the subject is stable) during the course of IL-1β antibody treatment (e.g., with the anti-IL-1β) antibody or fragment maintained at a constant dosing regimen). In another embodiment, treatment with the at least one active agent is reduced (e.g., tapered) or discontinued (e.g., when the subject is stable), and treatment with the anti-IL-1β antibody or fragment is reduced (e.g., lower dose, less frequent dosing, shorter treatment regimen). In another embodiment, treatment with the at least one active agent is reduced (e.g., tapered) or discontinued (e.g., when the subject is stable), and treatment with the anti-IL-1β antibody or fragment is increased (e.g., higher dose, more frequent dosing, longer treatment regimen). In yet another embodiment, treatment with the at least one active agent is maintained and treatment with the anti-IL-1β antibody or fragment is reduced or discontinued (e.g., lower dose, less frequent dosing, shorter treatment regimen). In yet another embodiment, treatment with the at least one active agent and treatment with the anti-IL-1β antibody or fragment, are reduced or discontinued (e.g., lower dose, less frequent dosing, shorter treatment regimen).

In some embodiments, reducing the treatment with at least one active agent (e.g. other than anti-IL-1β antibody or binding fragment) is reduction in the cumulative amount of active agent administered during a course of treatment. In some embodiments, reducing the treatment with at least one active agent (e.g., other than anti-IL-1β antibody or binding fragment) is a reduction in the actual dose amount of active agent administered. In some embodiments, reducing the treatment with at least one active agent provides a reduction in systemic immunosuppression.

The pharmaceutical compositions used in the disclosure may include a therapeutically effective amount or a prophylactically effective amount of the IL-1β binding antibodies or binding fragments. A therapeutically effective amount refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A prophylactically effective amount refers to an amount effective, at dosages and for periods of time necessary, to achieve the desired prophylactic result.

A therapeutically or prophylactically effective amount of a pharmaceutical composition comprising an IL-1β binding antibody or fragment will depend, for example, upon the therapeutic objectives such as the indication for which the composition is being used, the route of administration, and the condition of the subject. Pharmaceutical compositions are administered in a therapeutically or prophylactically effective amount to treat an IL-1 related condition.

Methods of Use

Anti-IL-1β binding antibodies or binding fragments thereof in a therapeutically effective amount may be used as disclosed herein for the treatment and/or prevention of uveitis, including, for example, refractory uveitis. The present disclosure also contemplates the use of other IL-1 pathway inhibitors, as an alternative or in addition to the anti-IL-1β antibodies or fragments.

The terms "prevention", "prevent", "preventing", "suppression", "suppress", "suppressing", as used herein with respect to the methods as described refer to preventing, suppressing, delaying or reducing, either temporarily or permanently, either partially or completely, the onset of a clinical symptoms or manifestation of an event, disease or condition (e.g., in an at risk subject, in a subject with a history of a prior event, disease or condition), such as, for example, uveitis (e.g., acute uveitis exacerbation). Such preventing or suppressing need not be absolute to be useful.

The terms "treatment", "treat" and "treating" as used with respect to methods as described herein refer to eliminating, reducing, suppressing or ameliorating, either temporarily or permanently, either partially or completely, a clinical symptom, manifestation or progression of an event, disease or condition (e.g., diagnosed symptom, manifestation or progression of an event, disease or condition), such as, for example, uveitis (e.g., acute uveitis exacerbation). Such treating need not be absolute to be useful.

The terms "inhibit", "inhibiting" and "inhibition" as used herein with respect to the methods as described refer to preventing, delaying, suppressing, reducing, treating, eliminating or ameliorating, either temporarily or permanently, either partially or completely, a clinical symptom or manifestation of an event, disease or condition, such, as, for example, uveitis (e.g., acute uveitis exacerbation). Such preventing, treating, suppressing or reducing need not be absolute to be useful.

The term "in need of treatment" as used herein refers to a judgment made by a caregiver that a patient requires or will benefit from treatment. This judgment is made based on a variety of factors that are in the realm, of a caregiver's expertise, but that includes the knowledge that the patient is ill, or will be ill, as the result of a condition that is treatable by a method or compound of the disclosure.

The term "effective amount" as used herein refers to an amount of a compound (e.g., IL-1β antibody), either alone or as a part of a pharmaceutical composition, that is capable of having any detectable, positive effect on any symptom, aspect, parameter or characteristics of a disease state or condition when administered to a subject (e.g., as one or more doses), including, for example, improving a uveitis parameter as referred to herein. Such effect need not be absolute to be beneficial.

The terms "treatment refractory" and "treatment resistant" uveitis as used herein refers to chronic or recurrent uveitis (e.g., acute uveitis exacerbation, uveitis flare) in a subject who has received prior treatment for the uveitis with one or more pharmaceutical compositions including, for example, a non-steroid immunosuppressant, a non-steroid anti-inflammatory or a steroid, but not including an IL-1β antibody or binding fragment. Treatment refractory and treatment resistant uveitis includes uveitis in a subject, wherein the subject may have had an adverse reaction or hypersensitivity to the prior treatment, or alternatively or in addition, the subject may have failed or partially responded to the prior treatment (e.g., inadequate or partial therapeutic effect, inadequate response, insufficient response, incomplete response, partial response).

The terms "reduction in the dosage", "reduction in dosage", "dosage reduction" and "reduced dosage" as used herein refers to a change in a prevention or treatment regimen for a pharmaceutical composition, as compared to a previous prevention or treatment regimen for the same pharmaceutical composition (e.g., prior to administering an anti-IL-1β antibody or binding fragment thereof). Preferably, such change in prevention or treatment regimen is a decrease in some aspect of the prevention or treatment regimen, such as for example, a decrease (e.g., reduction) in the dose (e.g., amount), a decrease (e.g., reduction) in the frequency of doses, or a decrease (e.g., reduction) in the cumulative exposure (e.g., area under the curve, AUC) over a period of time. Such change in prevention or treatment regimen for a pharmaceutical composition may be a change in a prevention, or treatment regimen as compared to a previous prevention or treatment regimen in the same subject, or alternatively or in addition, a change in a prevention or treatment regimen for a pharmaceutical composition when used concurrently with an anti-IL-1β antibody or binding fragment thereof as compared when not used concurrently with an anti-IL-1β antibody or binding fragment thereof.

The terms "acute uveitis exacerbation" as used herein refers to an occurrence of one or more clinical symptoms or manifestations (e.g., parameters) of uveitis in a subject. Alternatively or in addition, the subject may be a subject (e.g., at risk subject) that has previously experienced one or more clinical symptoms or manifestations (e.g., parameters) of uveitis, with an intervening period of clinically significant improvement in one or more uveitis symptoms (e.g., decrease and/or clinical control of symptoms, symptom free interval). For example, the acute uveitis exacerbation may be a first uveitis exacerbation or may be a re-occurrence of a uveitis exacerbation. The one or more uveitis symptoms during the acute uveitis exacerbation may be similar to, the same as, or different from (e.g., different combination) one or more uveitis symptoms experienced previously. A uveitis flare may be considered an acute uveitis exacerbation.

A variety of methods and techniques for detecting the presence of and/or changes in symptoms, aspects, parameters or characteristics of disease states or conditions referred to herein are known and accepted by those of skill in the art. Representative examples of uveitis parameters (e.g., symptoms) that may be examined for changes, such as for example, in the methods of treating or preventing uveitis of the present disclosure, may include any or all of visual acuity, vitreous haze, anterior chamber cell score, macular edema, laser flare cell count (e.g., flare score), subretinal pooling, epiretinal membrane formation, hypopyon, subretinal neovascularization, optic disc neovascularization, retinal neovascularization, retinal vasculitis, occlusive vasculitis, peripheral vascular sheathing, inflammatory sheathing, branch retinal vein occlusion, vascular leakage (e.g., fundus fluorescein angiography leakage score, dual fluorescein angiography and indocyanine green angiography score), optic disc hyperfluorescence, disc margin staining, optic disc leakage, cystic pooling, posterior pole arcades, retinal capillary nonperfusion, macular ischemia, pinpoint leaks, retinal staining, iritis, iridocyclitis, anterior cyclitis, pars planitis, posterior cyclitis, focal choroiditis, multifocal choroiditis, diffuse choroiditis, chorioretinitis, retinochoroiditis, retinitis, neuroretinitis, retinal dysfunction and elevated intraocular pressure.

Examination for changes (e.g., improvement) may be made by standard medically accepted practices known in the art, such as for example, detailed ophthalmological assessment comprising measurements of visual acuity (e.g., BCVA by ETDRS), intraocular pressure, and vitreous haze; evaluation of retinal findings (infiltrates, inflammatory sheathing, hemorrhages/occlusive vasculitis, and branch retinal vein occlusion); biomicroscopy (e.g., slit-lamp biomicroscopy); ophthalmoscopy (e.g., indirect ophthalmoscopy of the posterior segment followed by fundus photography), readings of laser flare cell photometry to track changes in visual acuity and other ocular components inflammation); fluorescein angiography (e.g., fundus fluorescein angiographic examination, dual fluorescein, angiography (FA) and indocyanine green angiography (ICGA)).

The clinical status of a subjects uveitis may be measured using the Uveitis Scoring System (BenEzra, et al., *Uveitis Scoring System*, Springer-Verlag, Berlin, 1991), which separates the assessment of uveitis into five components: anterior segment, vitreous, fundus, visual acuity, and fluorescein angiography. This system emphasizes the importance of the first three components in tracking intraocular inflammation. Components are scored separately, not cumulatively, for example:

The anterior segment is graded with slit-lamp biomicroscopy. Both cells and flares are graded from nil to severe.

Vitreous haze resulting from inflammation is examined with a binocular indirect ophthalmoscope, Scores range from nil to severe depending on the visibility of the posterior pole.

The fundus is graded according to a diagram that divides each eye into quadrants (e.g., four pre-equatorial and four post-equatorial sections) and examines each section for retinal vasculitis, chorioretinal lesions, and neovascularization of the disc.

Visual acuity scores are expressed in the decimal versions of standard fractions using either Snellen or ETDRS testing charts.

Fluorescein angiograms help to determine the extent of retinal inflammation. Diagrammatically dividing the eye into the quadrants (e.g., four pre- and post-equatorial segments) used previously for grading the fundus, the BenEzra system assesses the inflammation of each section according to 11 criteria.

In some embodiments, methods of the present disclosure may provide an improvement in Ben Ezra score, as measured by the Uveitis Scoring System. For example, the methods may provide an improvement (e.g., decrease) in score of 1 or more, 2 or more, 3 or more, 4 or more, 5 or more, 6 or more, 7 or more, 8 or more, 9 or more, or 10 or more. Alternatively or in addition, the methods of the present disclosure may provide an improvement in Ben Ezra score from any score greater than 0 to a score of 0.

In some embodiments, visual acuity (e.g., best corrected visual acuity, BCVA) may be measured (e.g., graded) using standard Bailey-Lovie logMAR, Snellen or ETDRS testing charts, which provide for objective measurements. For example, the methods of the present disclosure may provide at least a 1 line, at least a 2 line, at least a 3 line, at least a 4 line or at least a 5 line improvement in visual acuity as measured by a Snellen chart, test and/or as illustrated in the following table.

| Visual/Acuity in Different Notations | | | |
| --- | --- | --- | --- |
| Feet | Meters | Decimal | Jaeger |
| 20/20 | 6/6 | 1.0 | J1+ |
| 20/25 | 6/7.5 | 0.8 | J1 |
| 20/30 | 6/9 | 0.7 | J2 |
| 20/40 | 6/12 | 0.5 | J3 |
| 20/60 | 6/15 | 0.4 | J6 |
| 20/70 | 6/21 | N/A | J7 |
| 20/80 | 6/24 | N/A | N/A |
| 20/100 | 6/30 | 0.2 | J10 |
| 20/150 | 6/45 | N/A | N/A |
| 20/200 | 6/60 | 0.1 | J16 |
| 20/400 | 6/120 | 0.06 | N/A |

Alternatively of in addition, the methods of the present disclosure may provide at least a 1 line (e.g., 5 letter), at least a 2 line (e.g., 10 letter), at least a 3 line (e.g., IS letter), at least a 4 line (e.g., 20 letter), or at least a 5 line (e.g., 25 letter) improvement in visual acuity as measured by ETDRS chart (Ferris et al., 1982, Am. J. Ophthalmol., 94:91-6). In some embodiments, if the subject's visual acuity is so poor that the largest chart letters cannot be read when tested at one meter, then the subject's ability to count lingers, detect, hand motion, or have light perception may be evaluated.

Anterior chamber cell findings may be assessed using the SUN Working Group Grading Scheme (Jabs, et al., *Am J Ophthalmol.* 140:509-16, 2005). In some embodiments, the anterior segment may be assessed by biomicroscopy (e.g., slit-lamp biomicroscopy) and anterior chamber cell score may be measured (e.g., scored). In some embodiments, anterior chamber cells are scored using the SUN Working Group grading scheme, as shown below.

For example, the methods of the present disclosure may provide an improvement in anterior chamber cell score of at least 1 grade (e.g., 3+ to 2+, 1+ to 0.5+), at least 2 grades, at least 3 grades or at least 4 grades. Alternatively or in addition, the methods of the present disclosure may provide an Improvement in anterior chamber cell score from any of grades 1+ through 4+ to grade 0.5+ or better. Alternatively or in addition, the methods of the present disclosure may provide an improvement In anterior chamber cell score from any of grades 0.5+ through 4+ to grade 0.

| The SUN Working Group Grading Scheme for Anterior Chamber Cells | |
|---|---|
| Grade | Cells in Field[2] |
| 0 | <1 |
| 0.5+ | 1-5 |
| 1+ | 6-15 |
| 2+ | 16-25 |
| 3+ | 26-50 |
| 4+ | >50 |

[2]Field size is a 1 mm by 1 mm slit beam

In some embodiments, laser flare cell count (e.g., flare score), may be measured using laser flare-cell photometry, such as for example as described by Ladas et al., (Survey of Ophthalmology, 50: 27-47, 2005). For example, the methods of the present disclosure may provide an improvement (e.g., reduction) in laser flare cell count (e.g., flare score) of at least 10%, at least 20%, at least 30%, at least 40%, at least 50%, at least 60%, at least 70%, at least 80% or more, as compared to initial (e.g., pre-treatment) levels. Alternatively or in addition, the methods of the present disclosure may provide an improvement (e.g., reduction) in laser flare cell count (e.g., flare score), of at least a decrease in score of 10 or more, 29 or more, 30 or more, 40 or more, 50 or more, 60 or more, 70 or more, 80 or more, 90 or more, or 100 or more.

In some embodiments, vitreous haze may be measured using standard methods, such as for example by ophthalmoscopy (e.g., with binocular indirect ophthalmoscope), with grading, for example, according to the Nussenblatt classification (Nussenblatt et al., 1985, Ophthalmol. 92:467-71) and/or SUN Working Group's adaptation of the National Eye Institute system, for grading vitreous haze (Jabs et al, 2005, Am. J. Ophthalmol. 140:5009-16). For example, the methods of the present disclosure may provide an improvement (e.g., reduction) in vitreous haze of at least 1 grade (e.g., 3+ to 2+, 1+ to 0.5+), at least 2 grades, at least 3 grades or at least 4 grades. Alternatively or in addition, the methods of the present disclosure may provide an improvement in vitreous haze from any of grades 1+ through 4+ to grade 0.5+ or better. Alternatively or in addition, the methods of the present disclosure may provide an improvement in vitreous haze from any of grades 0.5+ through 4+ to grade 0.

Additional scoring measurements that may optionally be evaluated, such as for example, dual fluorescein angiography (FA) and indocyanine green angiography (ICGA), which may include for FA—optic disc hyperfluorescence, macular edema, retinal vascular staining and/or leakage, capillary leakage, retinal capillary nonperfusion, neovascularization of the optic disc, neovascularization elsewhere, pinpoint leaks, and retinal staining and/or subretinal pooling, and for ICGA—early stromal vessel hyperfluorescence, choroidal vasculitis, dark dots or areas (excluding atrophy), and/or optic disc hyperfluorescence, are defined by the Angiography Scoring for Uveitis Working Group (Tugai-Tutkun et al., *Int Ophthalmol* 2010 30(5):529-552; Epub ahead of print 2008 Sep. 16).

In some embodiments, intraocular pressure may be assessed using standard accepted medical practices, such as for example by Goldmann Tonometry. Vascular and/or neurological complications also may be followed. For example, subjects with organ involvement such as arterial, aneurysms or deep vein thrombosis, clinical findings may be followed and contrast-enhanced spiral computer tomography (CT) imaging may be performed. For subjects with parenchymal neurologic involvement, a complete neurologic examination, a contrast-enhanced cranial magnetic resonance imaging (MRI) and/or a cerebrospinal fluid (CSF) analysis may be performed.

Alternatively, or in addition, the following may be evaluated:

Color fundus photography. Color fundus photography is useful in documenting the presence of posterior-segment pathology. Color photography can often highlight subtle clinical findings, and it is especially useful for establishing 8 baseline and detecting disease progression over time.

Fluorescein angiography. Fluorescein angiography (FA) is useful in evaluating changes such as breakdown in the blood-retinal barrier, which can lead to CME and papillitis. FA is also useful in detecting vascular occlusion from vasculitis, which can be the result of the numerous causes of posterior uveitis and choroiditis, as well as complications such as retinal or choroidal neovascularization (CNV).

Indocyanine green angiography. Indocyanine green (ICG) angiography is used mainly as an adjunct to FA to help evaluate the choroidal vasculature. The most useful information is obtained in the later phases of the ICG study. Herbort and colleagues developed in 1997 a standardized protocol for administration, and interpretation of posterior uveitis using ICG. Several conditions, such as birdshot retinochoroiditis, are much more prominent with ICG angiography.

Autofluorescence. Autofluorescence (AF) imaging highlights the presence of lipofusion in the retinal pigment epithelium (RPE). Since many posterior uveitic conditions, particularly the white spot syndromes, affect the outer retina-RPE-choriocapillaries complex, AF can be a particularly useful noninvasive diagnostic tool. For Instance, the numerous dots and spots of MEWDS are much easier to appreciate with fundus AF.

B-scan ultrasonography. B-scan ultrasonography has been most useful in the evaluation of intraocular disorders associated with opacified media. Opacified media can he caused by intraocular inflammation and its complications, as well as other conditions, including: but not limited to corneal opacification, anterior chamber hyphema or hypopyon, posterior synechiae with miosis, cataract, vitreous hemorrhage, and retinal detachment. Ultrasound can also be used to evaluate inflammatory Infiltration of the choroid, as occurs in chronic uveitis including Vogt-Koyanagi-Harada (VKH) syndrome, sympathetic ophthalmia, and combined scleral and choroidal thickening from scleritis. In these situations, ultrasound becomes useful in evaluating patients prior to instituting therapy or planning surgery. In the presence of clear media, high-frequency ultrasound or ultrasound, biomicroscopy (UBM) can be of additional use, particularly for examination of the region of the ciliary body and pars plana, which are often involved in patients with intermediate uveitis and can be difficult to visualize clinically. UBM may also identify occult foreign bodies in cases of chronic uveitis occurring after trauma.

Optical coherence tomography. Optical coherence tomography (OCT) is currently one of the most important imaging techniques used in the study of uveitis, it enables imaging of the optic nerve head, nerve fiber layer; retina, choroid, and the vitreoretinal interface in a noncontact and noninvasive manner, it can be repeated as often as necessary since there are no serious side effects in OCT testing. OCT can be used to quantify macular thickening and thus is an excellent way of diagnosing CME and monitoring the effectiveness of treatment. OCT can detect vitreoretinal interface disorders such as epiretinal membranes, macular holes, and vitreomacular traction, which can assist in management. OCT is also valuable in the study of the different types of retinal detachment and the role, location, and density of an associated exudate. The most important limitation of OCT is its reliance on relatively clear media for useful images. A second factor limiting OCT's utility is the need for patient cooperation with fixation and control of eye movements. These limitations may prove difficult for photophobic subjects.

In some embodiments, methods of the present disclosure may provide an improvement Ben Ezra score, as measured by the Uveitis Scoring System (BenEzra, et al., *Uveitis Scoring System*, Springer-Verlag, Berlin, 1991). For example, the methods may provide an improvement (e.g., decrease) in score of 1 or more, 2 or more, 3 or more, 4 or more, 5 or more, 6 or more, 7 or more, 8 or more, 9 or more, or 10 or more. Alternatively or in addition, the methods of the present disclosure may provide an improvement in Ben Ezra score from any score greater than 0 to a score of 0.

Alternatively or in addition, assessments of other Behçet's disease parameters also may be performed.

Alternatively or in addition, assessments may include measures of biologic and clinical activity, including non-ocular parameters, such as for example:

Inflammatory markers (both CRP and ESR)

Analysis of cytokines (e.g., markers for cytokines, such as inflammatory cytokines), including, but not limited to, adiponectin, resistin, leptin, visfatin, PAI-1, TNFα, IFNγ, IL-1, IL-1Ra, IL-6, IL-8, RANTES, IL-1α and MCP-1.

In addition, methods of the present disclosure may provide an improvement (e.g., decrease) in C-reactive protein (CRP) levels. The reduction in CRP levels is readily measured using standard assays (e.g., high-sensitivity CRP, ultra-sensitive CRP). As provided by the methods disclosed herein, the decrease in C-reactive protein levels may, for example, be a decrease of ≥0.2, ≥0.4, ≥0.6, ≥0.8, ≥1.0, ≥1.4, ≥1.8, ≥2.2, ≥2.6, ≥3.0 mg/L from pre-treatment levels. Alternatively, the decrease in C-reactive protein levels may, for example, be a decrease of >20%, >30%, >40%, >50%, >60%, >70%, >80%, >90%, >95% from pre-treatment levels.

Further, the methods of the present disclosure may provide an improvement in one or more aspects of quality of life, such as for example as determined by a quality of life (QOL) assessment (e.g., SF-36V2 Health Survey, ophthalmological QOL questionnaire).

In some embodiments, methods of treating or preventing a disease or condition in accordance with the present disclosure may use a pre-determined or "routine" schedule for administration of the antibody or fragment. As used herein a routine schedule refers to a predetermined designated period of time between dose administrations. The routine schedule may encompass periods of time which are identical or which differ in length, as long as the schedule is predetermined. Any particular combination would be covered by the routine schedule as long as it is determined ahead of time that the appropriate schedule involves administration on a certain day.

EXAMPLES

The following examples are intended merely to further illustrate the practice of the present invention, but should not be construed as in any way limiting its scope. The disclosures of ail patent and scientific literatures cited within are hereby expressly incorporated in their entirety by reference.

Example 1

Clinical Study to Evaluate Treatment of Refractory Uveitis with an IL-1β Antibody A clinical trial was undertaken to evaluate treatment with an IL-1β antibody in human subjects diagnosed with uveitis (e.g., acute uveitis exacerbation). More specifically, an open label clinical study was performed to examine the safety, PK and clinical activity of a high affinity IL-1β antibody in subjects with uveitis refractory (e.g., resistant) to one or more standard of care medications, such as for example, non-steroid immunosuppressants (e.g., azathioprine, colchicine, cyclosporine, mycophenolate) and/or steroids (e.g., prednisolone). Multiple uveitis parameters were measured in this clinical study.

Subjects enrolled in the clinical trial included those with a uveitis exacerbation having at least acute posterior or panuveitis or retinal vasculitis, and who were also diagnosed with Behçet's disease fulfilling the international Study Group Classification Criteria. Additional criteria for entry into the trial also included:

Resistant to azathioprine, colchicine, and/or cyclosporine treatment

Receiving stable doses of azathioprine (2 mg/kg) and/or a stable cyclosporine treatment regimen for at least 1.4 days prior to Day 0

Agreement to discontinue any azathioprine, colchicine, and/or cyclosporine treatment on Day 0 and for duration of study Subjects were excluded from this study if they met any of the following criteria:

Severe uveitis and a potential visual acuity of less than 0.1 according to Snellen/ETDRS standards for visual acuity Subject has cataract and an assessment of the posterior segment of his or her uvea was poor or impossible Use of the following medications:
NSAID therapy (other than aspirin≤100 mg/day) from 28 days prior to Day 0 through the end of the study
Steroids>10 mg/day from 28 days prior to Day 0 through the end of the study, with subsequent protocol amendment to allow participation of one subject receiving prednisolone at 20 mg/day
interferon from 28 days prior to Day 0 through the end of the study The primary outcome measure was the severity of a subject's uveitis at Days 0 and 28, including degree of improvement in visual acuity and other ocular components (e.g., measured using the Ben-Ezra uveitis scoring system and laser flare meter readings), with periodic follow-up assessments through Day 98.

The prior treatment profiles of seven patients enrolled in this open-label study are shown in FIG. 1. All subjects had received prior treatment with azathioprine (AZA) and steroid, and additionally, some subjects had received prior treatment with colchicine and/or cyclosporine (CysA). Dose amounts for steroid treatment with prednisolone or methylprednisolone are converted to the prednisolone (PRD in FIG. 1) equivalent (e.g., 8 mg methylprednisolone=10 mg prednisolone; 16 mg methylprednisolone=20 mg prednisolone) in the Figure. Subjects continued steroid treatment through the study at the indicated prednisolone dose amounts unless a bolus administration was required at a later time point (post-28 day) as rescue medication.

A single dose of the IL-1β antibody AB7 was administered intravenously to the enrolled subjects at a dose of 0.3 mg/kg. Subjects underwent periodic follow-up assessment. Safety was assessed by pre- and post-treatment serial measurements of vital signs, clinical laboratory assessments, and the recording of adverse clinical events. PK data was collected and analyzed. Changes in the clinical status of the uveitis were evaluated to gauge long-term and average disease control, using an approach similar to Sfikakis et al. (*Lancet* 28:358, 2001). Because the study included subjects whose uveitis symptoms have not already responded to azathioprine, cyclosporins, and/or colchicine (e.g., treatment refractory), and who suspend these treatments during the course of the study, a rapid improvement in subject eye disease in the course of this trial would be attributable to study drug.

The primary outcome measure was the progress of uveitis from Day 0 to Day 28, with periodic follow-up assessments through Day 98. The clinical assessment of uveitis was assessed at every clinic visit (e.g. days 0, 1, 4, 7, 14, 21, 28, 56, 98) by standard medically accepted practices known in the art, such as for example, detailed ophthalmological assessment comprising measurements of visual acuity, intraocular pressure, and vitreous haze; an evaluation of retinal findings (infiltrates, inflammatory sheathing, hemorrhages/occlusive vasculitis, and branch retinal vein occlusion); slit-lamp biomicroscopy; and indirect ophthalmoscopy of the posterior segment followed by fundus photography. Readings of the laser flare cell photometry was recorded to track changes in visual acuity and other ocular components. At Days 0 (pre-dose) and Day 98 only, a fundus fluorescein angiographic examination also was performed.

The clinical status of a subject's uveitis was measured using the Uveitis Scoring System (BenEzra, et al., *Uveitis Scoring System*, Springer-Verlag, Berlin, 1991). The BenEzra uveitis scoring system separates the assessment of uveitis into five components as follows: anterior segment, vitreous, fundus, visual acuity, and fluorescein angiography. The system emphasizes the importance of the first three components in tracking intraocular inflammation. Components are scored separately, not cumulatively.

The anterior segment is graded with slit-lamp biomicroscopy. Both cells and flares are graded from nil to severe.

Vitreous haze resulting from inflammation is examined with a binocular indirect ophthalmoscope. Scores range from nil to severe depending on the visibility of the posterior pole.

The fundus is graded according to a diagram that divides each eye into four sections and examines each section for retinal vasculitis, chorioretinal lesions, and neovascularization.

Visual acuity scores are expressed in the decimal versions of standard fractions using either Snellen or ETDRS testing charts.

Fluorescein angiograms help to determine the extent of retinal inflammation. Diagrammatically dividing the eye into the four segments used previously for grading the fundus, the BenEzra system assesses the inflammation of each section according to 11 criteria.

In addition, anterior chamber cell findings were assessed using the SUN Working Group Grading Scheme (Jabs, et al., *Am J Ophthalmol* 140:509-16, 2005), as follows.

| The SUN Working Group Grading Scheme for Anterior Chamber Cells | |
|---|---|
| Grade | Cells in Field[2] |
| 0 | <1 |
| 0.5+ | 1-5 |
| 1+ | 6-15 |
| 2+ | 16-25 |
| 3+ | 26-50 |
| 4+ | >50 |

[2]Field size is a 1 mm by 1 mm slit beam

Additional scoring measurements, such as with fluorescein angiography (FA) and indocyanine green angiography (ICGA) are defined by the Angiography Scoring for Uveitis Working Group (Tugal-Tutkun et al., *Int Ophthalmol*, 2010 30(5):539-352, Epub ahead of print 2008 Sep. 16). In appropriate subjects, the clinical protocol also provided for assessment of the following of vascular and/or neurological complications. For subjects with organ involvement such as arterial aneurysms or deep vein thrombosis, the protocol provided for clinical findings to be followed during each visit and contrast-enhanced spiral computer tomography (CT) imaging were performed at Day 0 (baseline) and Day 98. For subjects with parenchymal neurologic involvement, the protocol provided for a complete neurologic examination to be performed during each visit, and a contrast-enhanced cranial magnetic resonance imaging (MRI) and a cerebrospinal fluid (CSF) analysis to be performed at Day 0 (baseline), Day 28, and Day 98. Additional assessments included measures of biologic and clinical activity, including non-ocular parameters, such as for example:

Inflammatory markers (both CRP and ESR)

Analysis of cytokines, including, but not limited to, adiponectin, resistin, leptin, visfatin, PAI-1, TNFα, IFN-γ, IL-1, IL-1Ra, IL-6, IL-8, RANTES, IL-1α and MCP-1.

Additional assessments of other Behçet's disease parameters (e.g., non-ocular) also may be performed.

Example 2

Treatment of Refractory Uveitis with an IL-1β Antibody

Data obtained from the study described in Example 1 demonstrated a clinical benefit in the treatment refractory uveitis of all subjects, resulting from administration of the IL-1β antibody, with improvement in multiple parameters. FIGS. 2-8 show individual subject data, through the Day 98 time points, for the parameters of visual acuity, anterior chamber cell score, flare score, vitreous haze and Ben Ezra score. FIGS. 9 and 10 include images showing specific examples of resolution of a hypopyon and resolution of vitreous haze following treatment with the IL-1β antibody. Overall, in these subjects, findings of intraocular inflammation were resolved in all patients starting from Day 1 following infusion, and resolution of retinal findings and vitreous haze was achieved in 7-21 days.

Example 3

Treatment of Refractory Uveitis with an IL-1β Antibody

A follow up study is undertaken in subjects who were previously enrolled and treated In the study described in Examples 1 and 2. The preceding study included subjects whose uveitis symptoms had not already responded to one or more standard of care medications, including for example, azathioprine, cyclosporine, and/or colchicine (e.g., treatment refractory, treatment resistant), and these medications were excluded during the course of that study. In the study described in this Example, one or more standard of care medications, including for example, non-steroid immunosuppressants (e.g., azathioprine, cyclosporine, colchicine) and/or steroids (e.g., prednisone), are permitted concurrently with anti-IL-1β antibody treatment.

These subjects may receive additional administrations of an IL-1β antibody over an extended period (e.g., to evaluate the effect on preventing recurrence of an acute uveitis exacerbation). More specifically, an IL-1β antibody is administered to subjects on Days 0, 14, and 28, followed by dosing every 4 weeks for up to 2 years. Initially, all subjects receive an intravenous 0.3 mg/kg dose of AB7 on Day 0 and a subcutaneous 0.3 mg/kg dose on Days 14, 21, 56, and 84. After these first five doses, subjects who are stable will have their dose lowered (e.g., to 0.2 mg/kg) every four weeks for the next four doses. Subjects who remain stable after these four doses (e.g., at 0.2 mg/kg) will have their dose lowered again (e.g., to 0.1 mg/kg) for additional administration of antibody every four weeks.

If a subject experiences an acute exacerbation of uveitis (e.g., flare) or an Inadequate response to treatment after having received a dose at either of the lower dose levels (e.g., 0.1 or 0.2 mg/kg), steroids, such as prednisolone (oral or IV) may be administered as a bolus plus taper. In addition, the subject's next scheduled dose of IL-1β. antibody may be increased to either of the previous dose levels. Following such an increase in dose level, if the subject remains stable through four doses at the higher dose level, the dose level may again be reduced.

Subjects undergo periodic follow-up assessments for up to 111 weeks. Safety is assessed by pre- and post-treatment serial measurements of vital signs, clinical laboratory assessments, and the recording of adverse clinical events. PK data is collected and analyzed. Clinical progress of uveitis and any vascular/neurological complications are assessed as described previously. Changes in the clinical status of the uveitis in subjects diagnosed with Behçet's disease are evaluated to gauge long term and average disease control, using an approach similar to that used by Sfikakis et al. (*Lancet* 28:358, 2001). The primary outcome measure is the progress or stability of uveitis (e.g., preventing recurrence of acute uveitis exacerbation) during the 2 years of this extension study. The clinical assessment of uveitis (assessed at every clinic visit) includes a detailed ophthalmological assessment comprising measurements of visual acuity, and vitreous haze; an evaluation of fundus findings (infiltrates, inflammatory sheathing, hemorrhages/occlusive vasculitis, and branch retinal vein occlusion); slit-lamp biomicroscopy of the anterior segment; and indirect ophthalmoscopy of the posterior segment followed by fundus photography. Readings of the laser flare cell photometry are recorded to track changes in visual acuity and other ocular components. On Days 0, 112, 224, 330, 448, 560, 672, and 756, the ophthalmological assessment includes a fundus fluorescein angiographic examination to evaluate the extent of retinal inflammation. The clinical status of a subject's uveitis is measured and scored using the methods described previously.

In appropriate subjects, vascular and/or neurological complications are followed. For subjects with organ involvement such as arterial aneurysms or deep vein thrombosis, clinical findings are followed during, each visit and contrast-enhanced spiral CT imaging is performed as clinically indicated. For subjects with parenchymal neurologic involvement, a complete neurologic examination is performed during each visit, and a contrast-enhanced cranial MRI and a cerebrospinal fluid (CSF) analysis is performed as clinically indicated. Inflammatory markers (CRP, ESR, and cytokines) are collected as additional measures of the biological activity of the antibody.

Example 4

Inhibiting an Acute Uveitis Exacerbation with an IL-1β Antibody

Additional clinical trials may be performed, and may include for example, the same or alternative dosages and dosing regimens, longer treatment and/or observation periods, greater numbers of subjects per group, subjects (e.g., at risk subjects) not currently suffering from acute uveitis attack (e.g., acute uveitis exacerbation) but with prior history of one or more uveitis attacks (e.g., within previous 6 months, 12 months), subjects continuing treatment with standard of care or tapering doses of one or more additional active agents (e.g., non-steroid immunosuppressant, non-steroid anti-inflammatory, azathioprine, steroid) and subjects diagnosed with alternative forms of uveitis (e.g., non-infectious, infectious) and/or with one or more other diseases or conditions (e.g., Inflammatory diseases).

For example, a clinical trial is performed in patients (e.g., Behçet's disease patients) who have been diagnosed with a history of recurrent uveitis (e.g., refractory uveitis, resistant uveitis), and thus are at risk for additional uveitis exacerbations, in order to assess the therapeutic effect of treatment with an IL-1β antibody to inhibit an acute uveitis exacerbation (e.g., uveitis flare, severe exacerbation). Subjects (e.g., at risk subjects) with a history of recurrent uveitis (e.g., uveitis flare/exacerbation within 8 months, uveitis flare/exacerbation within 12 months, uveitis flare/exacerbation within 18 months), but not experiencing a current acute uveitis exacerbation (e.g., within previous 1 month, within previous 3 months) and who are currently stable on one or more standard of care medications, including for example, a non-steroid immunosuppressant (e.g., azathioprine, cyclosporine, mycophenolate, methotrexate) and/or steroids (e.g., prednisone, prednisolone), are enrolled in this clinical study.

Groups of subjects (e.g., ten subjects, twenty-five subjects, fifty or more subjects) continue to receive standard of care treatment and additionally receive monthly treatment with an IL-1β antibody (e.g., 0.03 mg/kg dose, 0.3 mg/kg dose, 1.0 mg/kg dose, 30 mg dose, 100 mg dose) or placebo via subcutaneous injection. Optionally, the subject may receive an initial dose of antibody that is higher (e.g., 2-fold more) and/or delivered by an alternative route (e.g., IV) compared to subsequent doses of antibody. Subjects are then monitored, for example as described herein (e.g., in previous examples), for an acute exacerbation of uveitis during the treatment period (e.g., 6 months treatment period, 12 months treatment period). An acute uveitis exacerbation "event" may include not only deterioration in one or more conditions (e.g., decrease in visual acuity, increase in vitreous haze, retinal infiltrates or vasculitis), but also initiation of one or more rescue medications (e.g., bolus steroid treatment, new immunosuppressive therapy).

Therapeutic effect of the IL-1β antibody treatment is determined by comparing the antibody and placebo treatment groups for number of subjects In the group experiencing an acute exacerbation of uveitis (e.g. within a specified time period) and/or the time to acute uveitis exacerbation.

Example 5

Treatment of Uveitis with an IL-1β Antibody

Tapering of Standard of Care Treatment with Pharmaceutical Composition

A clinical trial is performed in patients (e.g., Behçet's disease patients) who have been diagnosed with a history of recurrent uveitis (e.g., refractory uveitis, resistant uveitis), in order to assess the therapeutic effect of treatment with an IL-1β antibody, and the ability of the antibody to inhibit an acute uveitis exacerbation (e.g., uveitis flare). Subjects with a history of recurrent uveitis, currently receiving one or more standard of care medications, including for example, a non-steroid immunosuppressant (e.g., azathioprine) and/or a steroid (e.g., prednisolone), and who are experiencing an acute uveitis exacerbation, are enrolled in this clinical study. The enrollment criteria for an acute uveitis exacerbation may include any of the aforementioned parameters, such as for example vitreous haze (e.g., ≥1+, ≥2+), decrease in visual acuity attributed to the exacerbation (e.g., no better than 20/40 ETDRS BCVA, ≥15-letter ETDRS or 2-line Snellen decrease), or retinal infiltrates and/or retinal vasculitis.

All subjects continue to receive standard of care treatment and additionally Initiate treatment with an IL-1β antibody (e.g., 0.03 mg/kg dose, 0.3 mg/kg dose, 1.0 mg/kg dose, 30 mg dose, 100 mg dose) via intravenous or subcutaneous administration to resolve the acute exacerbation. A second, optional dose of antibody may be administered (e.g., intravenous, subcutaneous) at 14 days. Patients are monitored weekly for response to the IL-1β antibody treatment and at a predetermined time following a response (e.g., 1 week later), generally by day 28, all subjects that have responded to treatment are randomized into one of two groups, with the first group continuing to receive standard of care treatment plus the IL-1β antibody (e.g., monthly) and the second group continuing to receive standard of care treatment and additionally placebo. Optionally, the subject may receive the initial dose of antibody in an amount that is higher (e.g., 2-fold more) and/or delivered by an alternative route (e.g., IV) compared to subsequent doses of antibody.

Subjects (e.g., at risk subjects) are then monitored as described herein (e.g., in previous examples) for recurrence of an additional acute exacerbation of uveitis during the second phase of the treatment period (e.g., 6 months treatment period, 12 months treatment period). An acute uveitis exacerbation "event" may include not only deterioration in one or more conditions (e.g., decrease in visual acuity, increase in vitreous haze, retinal infiltrates or retinal vasculitis), but also initiation of one or more rescue medications (e.g., bolus steroid treatment, new immunosuppressive therapy). In addition, the dose level of one or more standard of care drugs, such as for example an immunosuppressant (e.g., azathioprine, cyclosporine, mycophenolate) and/or steroid (e.g., prednisone), may optionally be decreased or tapered during the treatment period. Therapeutic effect of the IL-1β antibody treatment in preventing further acute uveitis exacerbations is determined by comparing the antibody and placebo treatment groups for number of subjects In the group experiencing an acute exacerbation of uveitis (e.g., within a specified time period, upon a specified number of subjects in a group experiencing an exacerbation) and/or the time to acute uveitis exacerbation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise Indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Mo language in the specification should be construed as indicating any non-claimed element as essential to the practice of the invention.

Preferred embodiments of this invention are described herein, including the best mode known to the inventors for carrying out the invention. Variations of those preferred embodiments may become apparent to those working in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law,. Moreover, any combination of the above-described elements in all possible variations thereof is encompassed by the invention unless otherwise indicated herein or otherwise clearly contradicted by context.

The invention claimed is:

1. A method of treating uveitis in a subject, the method comprising administering to the subject an effective amount of anti-IL-1β antibody or antigen binding fragment thereof, wherein the uveitis is treatment refractory uveitis, wherein the subject has been diagnosed with Behçet's disease, and wherein the antibody or antigen binding fragment thereof binds to human IL-1β.

2. The method of claim 1, wherein treating uveitis in a subject is treating an acute uveitis exacerbation.

3. The method of claim 1, wherein said method of treating uveitis in a subject increases the interval between acute uveitis exacerbations.

4. The method of claim 1, wherein said method of treating uveitis in a subject decreases the frequency of acute uveitis exacerbations.

5. The method of claim 1, wherein said method of treating uveitis in a subject decreases the likelihood of experiencing an acute uveitis exacerbation.

6. The method of claim 1, wherein said method of treating uveitis in a subject prevents an acute uveitis exacerbation.

7. The method of claim 1, wherein said method of treating uveitis in a subject decreases the severity of an acute uveitis exacerbation.

8. The method of claim 1, wherein the treatment refractory uveitis is uveitis that is refractory to treatment with a pharmaceutical composition comprising a non-steroid immunosuppressant, a non-steroid anti-inflammatory or a steroid.

9. The method of claim 8, wherein the non-steroid immunosuppressant is a DNA synthesis inhibitor, a cyclosporine, a mycophenolate or a colchicine.

10. The method of claim 9, wherein the DNA synthesis inhibitor is azathioprine, an alkylating agent, an anti-metabolite, X-ray therapy, chlorambucil or cyclophosphamide.

11. The method of claim 8, wherein the non-steroid anti-inflammatory is a TNF inhibitor, an IL-6 inhibitor or an IL-17 inhibitor.

12. The method of claim 8, wherein the steroid is a steroid hormone selected from the group consisting of prednisone, methylprenisolone, prednisolone, a cortisol, an andrenocorticotrophic hormone and a glucocorticoid.

13. The method of claim 1, wherein the subject is receiving concurrently for the treatment of said uveitis one or two pharmaceutical compositions comprising a non-steroid immunosuppressant, a non-steroid anti-inflammatory or a steroid.

14. The method of claim 13, wherein the subject is receiving concurrently for the treatment of said uveitis one pharmaceutical composition comprising a non-steroid immunosuppressant, a non-steroid anti-inflammatory or a steroid.

15. The method of claim 1, wherein the subject is not receiving concurrently for the treatment of said uveitis a pharmaceutical composition selected from the group consisting of a pharmaceutical composition comprising a non-steroid immunosuppressant, a pharmaceutical composition comprising a non-steroid anti-inflammatory and a pharmaceutical composition comprising a steroid.

16. The method of claim 15, wherein the subject is not receiving concurrently for the treatment of said uveitis a pharmaceutical composition comprising a non-steroid immunosuppressant.

17. The method of claim 15, wherein the subject is not receiving concurrently for the treatment of said uveitis a pharmaceutical composition comprising a non-steroid anti-inflammatory.

18. The method of claim 15, wherein the subject is not receiving concurrently for the treatment of said uveitis a pharmaceutical composition comprising a steroid.

19. The method of claim 1, wherein the subject has received prior treatment for uveitis with one or more pharmaceutical compositions comprising a non-steroid immunosuppressant, a non-steroid anti-inflammatory or a steroid.

20. The method of claim 19, wherein the subject had an adverse reaction or hypersensitivity to said prior treatment of uveitis with one or more pharmaceutical compositions comprising a non-steroid immunosuppressant, a non-steroid anti-inflammatory or a steroid.

21. The method of claim 19, wherein the subject failed said prior treatment of uveitis with one or more pharmaceutical compositions comprising a non-steroid immunosuppressant, a non-steroid anti-inflammatory or a steroid.

22. The method of claim 1, wherein, the subject is receiving concurrently for the treatment of said uveitis at least one pharmaceutical composition comprising a non-steroid immunosuppressant, a non-steroid anti-inflammatory or a steroid, and wherein said method provides a reduction in the dosage of said at least one pharmaceutical composition.

23. The method of claim 22, wherein said reduction in the dosage is a reduction in the dose of said at least one pharmaceutical composition, as compared to the dose prior to administering the anti-IL-1β antibody or antigen binding fragment thereof.

24. The method of claim 22, wherein said reduction in the dosage is a reduction in the frequency of doses of said at least one pharmaceutical composition, as compared to the frequency of doses prior to administering the anti-IL-1β antibody or antigen binding fragment thereof.

25. The method of claim 22, wherein the dosage of a pharmaceutical composition comprising a non-steroid immunosuppressant is reduced.

26. The method of claim 25, wherein, the non-steroid immunosuppressant is a DNA synthesis inhibitor, a cyclosporine, mycophenolate or a colchicine.

27. The method of claim 26, wherein the DNA synthesis inhibitor is azathioprine or methotrexate.

28. The method of claim 22, wherein the dosage of a pharmaceutical composition comprising a steroid is reduced.

29. The method of claim 28, wherein the steroid is a steroid hormone selected from the group consisting of prednisolone, a cortisol, an andrenocorticotrophic hormone and a glucocorticoid.

30. The method of claim 22, wherein the dosage of a pharmaceutical composition comprising a non-steroid anti-inflammatory is reduced.

31. The method of claim 1, wherein said method results in an improvement in Ben-Ezra uveitis score.

32. The method of claim 1, wherein said method results in an improvement in anterior uveitis or posterior uveitis.

33. The method of claim 1, wherein said method results in an improvement in at least one or two parameters selected from visual acuity, vitreous haze, anterior chamber cell score, macular edema, laser flare cell count, subretinal pooling, epiretinal membrane formation, hypopyon, subretinal neovascularization, optic disc neovascularization, retinal neovascularization, retinal infiltrates, retinal vasculitis, occlusive vasculitis, peripheral vascular sheathing, inflammatory sheathing, branch retinal vein occlusion, fundus fluorescein angiography leakage score, optic disc hyperfluorescence, disc margin staining, optic disc leakage, cystic pooling, posterior pole arcades, retinal capillary nonperfusion, macular ischemia, pinpoint leaks, retinal staining, iritis, iridocyclitis, anterior cyclitis, pars planitis, posterior cyclitis, focal choroiditis, multifocal choroiditis, diffuse choroiditis, chorioretinitis, retinochoroiditis, retinitis, neuroretinitis, retinal dysfunction and elevated intraocular pressure.

34. The method of claim 33, wherein said method results in an improvement in at least two parameters selected from visual acuity, vitreous haze, laser flare-cell count and retinal vasculitis.

35. The method of claim 1, wherein the treatment refractory uveitis is non-infectious uveitis.

36. The method of claim 1, wherein the antibody or antigen binding fragment thereof binds to human IL-1β with a dissociation constant of about 1 nM or less, about 250 pM or less, about 50 pM or less, about 10 pM or less, or about 1 pM or less.

37. The method of claim 1, wherein the antibody or antigen binding fragment thereof binds to an epitope of IL-1β that is the same as the epitope bound by an antibody having the light chain variable region of SEQ ID NO:5 and the heavy chain variable region of SEQ ID NO:6.

38. The method of claim 1, wherein the antibody or antigen binding fragment thereof binds to an epitope incorporating Glu64 of IL-1β.

39. The method of claim 1, wherein the antibody or antigen binding fragment thereof binds to amino acids 1-34 of the N terminus of IL-1β.

40. The method of claim 1, wherein the antibody or antigen binding fragment thereof is administered in one or more doses of about 3 mg/kg or less, about 1 mg/kg or less, about 0.3 mg/kg or less, about 0.1 mg/kg or less, about 0.03 mg/kg or less, or about 0.01 mg/kg or less of antibody or fragment.

41. The method of claim 40, wherein the one or more doses are at least 0.01 mg/kg of antibody or antigen binding fragment thereof.

42. The method of claim 1, wherein the antibody or antigen binding fragment thereof is administered as a fixed dose, independent of a dose per subject weight ratio.

43. The method of claim 42, wherein the antibody or antigen binding fragment thereof is administered in one or more doses of 500 mg or less, 250 mg or less, 100 mg or less, 25 mg or less, 10 mg or less, or 0.1 mg or less.

44. The method of claim 42, wherein the antibody or antigen binding fragment thereof is administered in one or more doses of at least 1.0 mg of antibody or antigen binding fragment thereof.

45. The method of claim 1, wherein the anti-IL-1β antibody or antigen binding fragment thereof is administered by subcutaneous, intravenous, intraocular or intramuscular injection.

46. The method of claim 1, wherein administration of an initial dose of the antibody or antigen binding fragment thereof is followed by the administration of one or more subsequent doses, and wherein said one or more subsequent doses are in an amount that is approximately the same or less than the initial dose.

47. The method of claim 1, wherein administration of an initial dose of the antibody or antigen binding fragment thereof is followed by the administration of one or more subsequent doses, and wherein at least one of the subsequent doses is in an amount that is more than the initial dose.

48. The method of claim 1, wherein the anti-IL-1β antibody or antigen binding fragment thereof is administered in a dose amount and frequency sufficient to maintain a systemic trough serum concentration of at least about 0.5 μg/mL, at least about 1.0 μg/mL, or at least about 2.0 μg/mL.

49. A method of treating uveitis in a subject, the method comprising administering to the subject an effective amount of anti-IL-1β antibody or antigen binding fragment thereof, wherein the subject is receiving concurrently for the treatment of said uveitis one or two pharmaceutical compositions comprising a non-steroid immunosuppressant, a non-steroid anti-inflammatory or a steroid, wherein the uveitis is treatment refractory uveitis, wherein the subject has been diagnosed with Behçet's disease, and wherein the antibody or antigen binding fragment thereof binds to human IL-1β.

50. The method of claim 49, wherein the subject is receiving concurrently for the treatment of said uveitis one pharmaceutical composition comprising a non-steroid immunosuppressant, a non-steroid anti-inflammatory or a steroid.

51. A method of treating uveitis in a subject, the method comprising administering to the subject an effective amount of anti- IL-1β antibody or antigen binding fragment thereof, wherein the subject is not receiving concurrently for the treatment or prevention of said uveitis a pharmaceutical composition selected from the group consisting of a pharmaceutical composition comprising a non-steroid immunosuppressant, a pharmaceutical composition comprising a non-steroid anti-inflammatory and a pharmaceutical composition comprising a steroid, wherein the uveitis is treatment refractory uveitis, wherein the subject has been diagnosed with Behçet's disease, and wherein the antibody or antigen binding fragment thereof binds to human IL-1β.

52. A method of treating or preventing an acute uveitis exacerbation in a subject, the method comprising administering to the subject an effective amount of anti-IL-1β antibody or antigen binding fragment thereof, wherein the subject has received prior treatment for uveitis with one or more pharmaceutical compositions comprising a non-steroid immunosuppressant, a non-steroid anti-inflammatory or a steroid, wherein the uveitis is treatment refractory uveitis, wherein the subject has been diagnosed with Behçet's disease, and wherein the antibody or antigen binding fragment thereof binds to human IL-1β.

53. The method of claim 52, wherein the subject had an adverse reaction or hypersensitivity to, or failed said prior treatment of uveitis with one or more pharmaceutical compositions comprising a non-steroid immunosuppressant, a non-steroid anti-inflammatory or a steroid.

54. The method of claim 52, wherein said treating or preventing an acute uveitis exacerbation is an increase in the interval between acute uveitis exacerbations, a decrease in the frequency of acute uveitis exacerbations, a decrease in the likelihood of experiencing an acute uveitis exacerbation, preventing an acute uveitis exacerbation or decreasing the severity of an acute uveitis exacerbation.

55. A method of treating or preventing an acute uveitis exacerbation in a subject, the method comprising administering to the subject an effective amount of anti-IL-1β antibody or antigen binding fragment thereof, wherein the subject is receiving concurrent treatment for said uveitis with one or two pharmaceutical compositions comprising a non-steroid immunosuppressant, a non-steroid anti-inflammatory or a steroid, wherein the uveitis is treatment refractory uveitis, wherein the subject has been diagnosed with Behçet's disease, and wherein the antibody or antigen binding fragment thereof binds to human IL-1β.

56. The method of claim 55, wherein said treating or preventing an acute uveitis exacerbation is an increase in the interval between acute uveitis exacerbations, a decrease in the frequency of acute uveitis exacerbations, a decrease in the likelihood of experiencing an acute uveitis exacerbation, preventing an acute uveitis exacerbation or decreasing the severity of an acute uveitis exacerbation.

57. A method of treating uveitis in a subject, the method comprising administering to the subject an effective amount of anti-IL-1β antibody or antigen binding fragment thereof, wherein the subject is receiving concurrently for the treatment of said uveitis at least one pharmaceutical composition comprising a non-steroid immunosuppressant, a non-steroid anti-inflammatory or a steroid, and wherein said method provides a reduction in the dosage of said at least one pharmaceutical composition, wherein the uveitis is treatment refractory uveitis, wherein the subject has been diagnosed with Behçet's disease, and wherein the antibody or antigen binding fragment thereof binds to human IL-1β.

58. A method of treating uveitis in a subject, the method comprising administering to the subject an anti-IL-1β antibody or antigen binding fragment thereof in a dose amount and frequency sufficient to maintain a systemic trough serum concentration of at least about 0.5 μg/mL, at least about 1.0 μg/mL, or at least about 2.0 μg/mL, wherein the uveitis is treatment refractory uveitis, wherein the subject has been diagnosed with Behçet's disease, and wherein the antibody or antigen binding fragment thereof binds to human IL-1β.

59. A method of treating, suppressing, delaying, or reducing one or more symptoms of uveitis, the method comprising administering to the subject an effective amount of anti-IL-1β antibody or antigen binding fragment thereof, wherein the uveitis is treatment refractory uveitis, wherein the subject has been diagnosed with Behçet's disease, and wherein the antibody or antigen binding fragment thereof binds to human IL-1β.

60. The method of claim 59, wherein the treatment refractory uveitis is non-infectious uveitis.

61. The method of claim 59, wherein the antibody or antigen binding fragment thereof binds to human IL-1β with a dissociation constant of about 1 nM or less, about 250 pM or less, about 50 pM or less, about 10 pM or less, or about 1 pM or less.

62. The method of claim 59, wherein the antibody or antigen binding fragment thereof binds to an epitope of IL-1β that is the same as the epitope bound by an antibody having the light chain variable region of SEQ ID NO:5 and the heavy chain variable region of SEQ ID NO:6.

63. The method of claim 59, wherein the antibody or antigen binding fragment thereof binds to an epitope incorporating Glu64 of IL-1β.

64. The method of claim 59, wherein the antibody or antigen binding fragment thereof binds to amino acids 1-34 of the N terminus of IL-1β.

65. The method of claim 59, wherein the antibody or antigen binding fragment thereof is administered in one or more doses of about 3 mg/kg or less, about 1 mg/kg or less, about 0.3 mg/kg or less, about 0.1 mg/kg or less, about 0.03 mg/kg or less, or about 0.01mg/kg or less of antibody or fragment.

66. The method of claim 65, wherein the one or more doses are at least 0.01 mg/kg of antibody or antigen binding fragment thereof.

67. The method of claim 59, wherein the antibody or fragment is administered as a fixed dose, independent of a dose per subject weight ratio.

68. The method of claim 67, wherein the antibody or antigen binding fragment thereof is administered in one or more doses of 500 mg or less, 250 mg or less, 100 mg or less, 25 mg or less, 10 mg or less, or 0.1 mg or less of antibody or antigen binding fragment thereof.

69. The method of claim 67, wherein the antibody or antigen binding fragment thereof is administered in one or more doses of at least 1.0 mg of antibody or antigen binding fragment thereof.

70. The method of claim 59, wherein the anti-IL-1β antibody or antigen binding fragment thereof is administered by subcutaneous, intravenous, intraocular or intramuscular injection.

71. The method of claim 59, wherein administration of an initial dose of the antibody or antigen binding fragment thereof is followed by the administration of one or more subsequent doses, and wherein said one or more subsequent doses are in an amount that is approximately the same or less than the initial dose.

72. The method of claim 59, wherein administration of an initial dose of the antibody or antigen binding fragment thereof is followed by the administration of one or more subsequent doses, and wherein at least one of the subsequent doses is in an amount that is more than the initial dose.

73. The method of claim 59, wherein the antibody or antigen binding fragment thereof is administered in a dose amount and frequency sufficient to maintain a systemic trough serum concentration of at least about 0.5 μg/mL, at least about 1.0 μg/mL, or at least about 2.0 μg/mL.

* * * * *